United States Patent
Ichim et al.

(10) Patent No.: US 12,385,011 B2
(45) Date of Patent: Aug. 12, 2025

(54) TREATMENT OF HEART FAILURE AND/OR POST INFARCT PATHOLOGICAL REMODELING BY EX VIVO REPROGRAMMED IMMUNE CELLS

(71) Applicant: CREATIVE MEDICAL TECHNOLOGIES, INC., Phoenix, AZ (US)

(72) Inventors: Thomas Ichim, San Diego, CA (US); Amit Patel, Salt Lake City, UT (US)

(73) Assignee: Creative Medical Technologies, Inc., Phoenix, AZ (US)

( * ) Notice: Subject to any disclaimer, the term of this patent is extended or adjusted under 35 U.S.C. 154(b) by 358 days.

(21) Appl. No.: 17/559,970

(22) Filed: Dec. 22, 2021

(65) Prior Publication Data
US 2022/0202860 A1 Jun. 30, 2022

Related U.S. Application Data

(60) Provisional application No. 63/132,472, filed on Dec. 30, 2020.

(51) Int. Cl.
| | | |
|---|---|---|
| *A61K 35/17* | (2025.01) | |
| *A61K 40/11* | (2025.01) | |
| *A61K 40/40* | (2025.01) | |
| *A61P 9/04* | (2006.01) | |
| *C12N 5/0783* | (2010.01) | |

(52) U.S. Cl.
CPC ............ *C12N 5/0636* (2013.01); *A61K 40/11* (2025.01); *A61K 40/40* (2025.01); *A61P 9/04* (2018.01); *A61K 2239/31* (2023.05); *A61K 2239/38* (2023.05); *C12N 2502/1358* (2013.01)

(58) Field of Classification Search
None
See application file for complete search history.

(56) References Cited

U.S. PATENT DOCUMENTS

2014/0369983 A1* 12/2014 Sanberg .................... A61P 9/00
424/93.71
2017/0165194 A1* 6/2017 Meng .................... A61Q 19/00

FOREIGN PATENT DOCUMENTS

WO WO 2018/236988 12/2018

OTHER PUBLICATIONS

Mosterd, Arend et. al. Clinical Epidemiology of Heart Failure. Heart 2007;93:1137-1146 (Year: 2007).*
Myocarditis Foundation. Myocarditis Treament. pp. 1-2. (Year: 2024).*
Kaplan, Abdullah et al. Update on the Protective Role of Regulatory T Cells in Myocardial Infarction: A Promising Therapy to Repair the Heart. Journal of Cardiovasc Pharmacol (68): pp. 401-413. (Year: 2016).*
Amandda Évelin Silva-Carvalho, Mesenchymal stem cells immunomodulation: The road to IFN-y licensing and the path ahead, Cytokine and Growth Factor Reivews, 2019, 32-42, vol. 47.

* cited by examiner

*Primary Examiner* — Nghi V Nguyen
(74) *Attorney, Agent, or Firm* — Baumgartner Patent Law, LLC; Marc Baumgartner

(57) ABSTRACT

Disclosed are methods, means and compositions of matter useful for treatment of heart failure, and/or post infarct pathological remodeling using ex vivo reprogrammed immune cells. In one embodiment, cells of the recipient (autologous) are cocultured with a regenerative cell population alone or in the presence of one or more adjuvants. Said adjuvants enhance transfer of regenerative activity from said mesenchymal stem cells to said immune cells. In one embodiment said ex vivo reprogrammed immune cells are capable of inducing death or inactivation of cardiac fibrotic cells. In other embodiments, said immune cells provide antifibrotic activity to induce suppression of cardiac fibrosis. In other embodiments, said immune cells provide for growth factors to enhance cardiac regeneration.

8 Claims, 1 Drawing Sheet

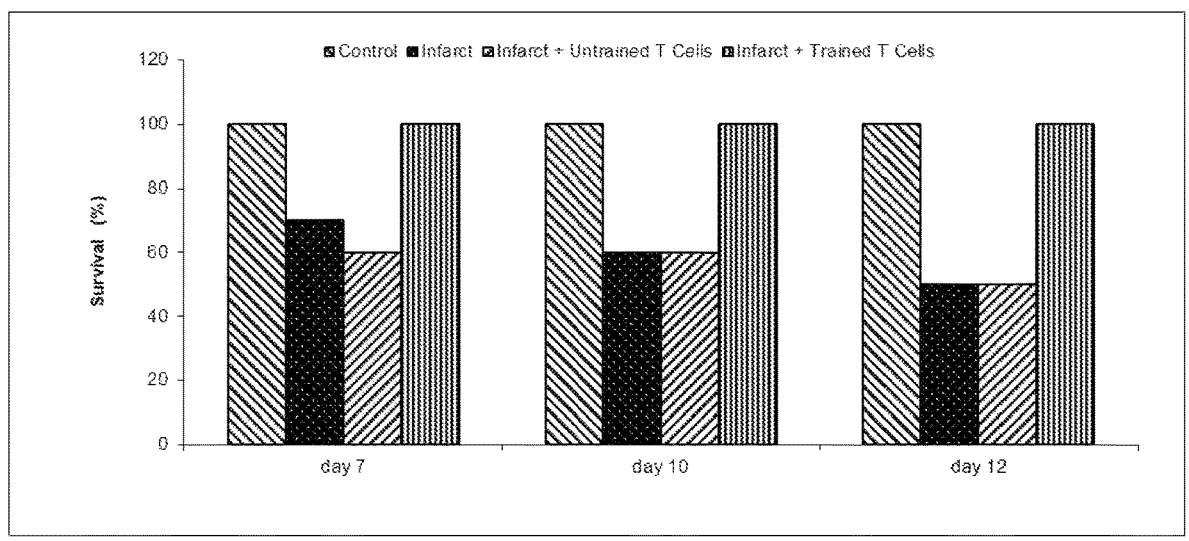

TREATMENT OF HEART FAILURE AND/OR POST INFARCT PATHOLOGICAL REMODELING BY EX VIVO REPROGRAMMED IMMUNE CELLS

CROSS-REFERENCE TO RELATED APPLICATIONS

This application claims priority to U.S. Provisional Application No. 63/132,472, filed Dec. 30, 2020, which is herein incorporated by reference in its entirety.

FIELD OF THE INVENTION

The invention pertains to the field of heart failure, more specifically the invention relates to treatment of heart failure with immune modulatory cells, more specifically, the invention relates to treatment of heart failure with ex vivo stem cell reprogrammed cells.

BACKGROUND OF THE INVENTION

It is known that despite the broad use of cholesterol lowering agents and better control of co-morbid illnesses (i.e. diabetes, hypertension, etc.) that contribute to ischemic cardiovascular disease, acute myocardial infarction remains common with a reported annual incidence of 1.1 million cases in the United States alone. Acute myocardial infarction causes necrotic and apoptotic myocardial cell death resulting in ventricular remodeling, which is a precursor to subsequent cardiac dysfunction, congestive heart failure and resulting cardiac related adverse events including death in a significant percentage of patients. The extent of myocardial cell loss is dependent on the location and duration of coronary artery occlusion, existing collateral coronary circulation and the condition of the cardiac microvasculature.

Myocardial cell loss along with evolving microvascular insufficiency and inadequate collateral circulation development can result in chronic hemodynamic overload and eventual congestive heart failure. Once developed the prognosis is poor with observed median survivals of 0.7 and 3.2 years in men and women, respectively. Thus, therapies are applied to limit or prevent ventricular remodeling in order to avoid left ventricular dilatation and late congestive heart failure after myocardial infarction.

Newer modalities resulting in immediate re-perfusion of occluded coronary arteries have been successful in limiting the extent of myocardial infarcts, ameliorating angina pectoris, improving function of remaining viable myocardium and limiting subsequent infarcts. Unfortunately, these interventions have not significantly altered the resulting cardiac dysfunction caused by myocardial cell loss and peri-infarct zone micro-vascular insufficiency. Myocardial cells have virtually no ability to regenerate, thus myocardial infarction leads to permanent cardiac dysfunction due to contractile-muscle cell loss and replacement with non-functioning fibrotic scaring. Moreover, compensatory hypertrophy of viable cardiac muscle leads to micro-vascular insufficiency that results in further demise in cardiac function by causing myocardial muscle hibernation and apoptosis of hypertrophied myocytes in the peri-infarct zone. Consequently, new strategies are in development to limit or prevent cardiac dysfunction after acute injury and to restore cardiac function in the chronic dysfunction setting.

In the setting of brief (3 to 5 minutes) coronary artery occlusion, energy metabolism is impaired leading to demonstrable cardiac muscle dysfunction that can persist for up to 48 hours despite immediate reperfusion. This so called stunned myocardium phenomenon occurs subsequent to reperfusion and is thought to be a result of reactive oxygen molecules. The process is transient and not associated with an inflammatory response. Immediately following a myocardial infarction, transient generalized cardiac dysfunction (stunned myocardium) uniformly occurs. After successful revascularization significant recovery from stunning occurs within three to four days, although complete recovery may take much longer.

Coronary artery occlusion of more significant duration leading to myocardial ischemia is associated with a significant inflammatory response that begins immediately after reperfusion and can last for up to several weeks. The inflammatory cascade following reperfusion is complex, initially contributing to myocardial damage but then later leading to healing and scar formation. This complex process appears to occur in two phases. In the first so called "hot" phase (within the first 5 days), reactive oxygen species in the ischemic myocardial tissue along with complement activation, generate a leukocyte chemotaxis signal and initiate a cytokine cascade. Mast cell degranulation, TNF alpha release and increased IL-6, ICAM-1, selectin (L, E and P) and integrin (CD 11a, CD 11b and CD 18) expression all appear to contribute to neutrophil accumulation and degranulation in ischemic myocardium. Neutrophils contribute significantly to myocardial cell damage and death through micro-vascular obstruction, and activation of neutrophil respiratory burst pathways after ligand-specific adhesion to cardiac myocytes (21). During the "hot" phase, angiogenesis is inhibited due to the release of angiostatic substances including Interferon gamma inducible protein (IP 10).

In the second phase, the cardiac repair process begins (days 7 to 14) that eventually lead to scar formation (days 14 to 21) and subsequent ventricular remodeling (days 21 to 90). Soon after reperfusion, monocytes infiltrate the infarcted myocardium. Attracted by complement (C 5a), TGF-B1 and MCP-1, monocytes differentiate into macrophages that initiate the healing process through scavenging dead tissue, regulating extracellular matrix metabolism and inducing fibroblast proliferation. Secretion of IL-10 by infiltrating lymphocytes also promotes healing by down-regulating inflammatory cytokines and influencing tissue remodeling. Mast cells appear to also be involved in the later stages of myocardial repair by participating in the formation of fibrotic scar tissue. Stem Cell Factor (SCF) is a potent attractor of mast cells. SCF mRNA has been shown to be up-regulated in ischemic myocardial segments in a canine model of myocardial infarction and thus may contribute to mast cell accumulation at ischemic myocardial sites. Excreted mast cell products (TGF-B, bFGF, VEGF and gelatinases A and B) induce fibroblast proliferation, influence extracellular matrix metabolism and induce angiogenesis.

Among survivors of myocardial infarction, residual cardiac function is influenced most by the extent of ventricular remodeling. Alterations in ventricular topography occur in both infarcted and healthy cardiac tissue after myocardial infarction. Specifically, ventricular dilatation causes a decrement in global cardiac function and is affected most by the infarct size, infarct healing and ventricular wall stresses. Recent efforts to minimize remodeling have been successful by limiting infarct size through rapid reperfusion using thrombolytic agents and mechanical interventions, along with reducing ventricular wall stresses by judicious use of pre-load therapies and proper after load management.

Regardless of these interventions, a substantial percentage of patients experience clinically relevant and long-term cardiac dysfunction after myocardial infarction.

In one study, improvement in left ventricular function was first evident seven days after primary angioplasty, becoming statistically significant at day 30 and continued to improve up to day 90 after which no further improvement was observed. In this study of 101 consecutive patients, recovery of left ventricular function was significantly improved only if the primary coronary angioplasty was performed within 4 hours of symptom onset. In fact, in the patient group who underwent angioplasty after 4 hours of symptom onset, no improvement in left ventricular function was observed. Thus, patients experiencing symptoms in excess of 4 hours would appear to be even more likely to develop chronic hemodynamic overload and are at a greater risk to develop late congestive heart failure.

In another study, regardless of the time to revascularization, serial MRI evaluations with baseline assessment performed after the "hot" stunned phase (4 to 7 days) showed no significant improvement in cardiac function at 3 and 6-month, follow-up (13). Moreover, in another study of 284 consecutive patients treated with primary percutaneous transangiography (PCTA), 85 patients (30%) had left ventricular dilatation at 6 months after AMI despite successful PCTA. The group with left ventricular dilatation at 6 months had significantly ($P=0.005$) greater cardiac deaths and other adverse cardiac events ($P=0.025$) compared with those without left ventricular dilatation at 6 months.

Collectively these data indicate that in addition to revascularization and medical interventions, new therapies intended to limit the rate and severity of left ventricular remodeling by altering infarct healing are needed. Limiting or preventing left ventricular remodeling has the potential to reduce subsequent left ventricular dilatation and chronic congestive heart failure. This would appear to hold promise to reduce the incidence of late cardiac related adverse events including deaths caused by ventricular remodeling after myocardial infarction.

Focal myocardial cell necrosis creates stress on global heart function, which is largely proportionate to the amount of myocardial cell loss. By limiting the amount of myocardial cell loss, rapid revascularization and proper medical management have reduced the incidence and extent of ventricular remodeling and subsequent adverse cardiac events including death. However, once lost there is little evidence that the body is capable of regenerating functioning myocardium, despite the presence of circulating progenitor cells that appear able to home to damaged myocardium and potentially, differentiate into myocardial and endothelial cells.

Recent data suggest that increased levels of circulating endothelial progenitor cells are a surrogate marker of better vascular function and lower cumulative cardiovascular risk. Endothelial cells appear to be capable of migrating to and accumulating at sites of damaged blood vessel wall endothelium, resulting in endothelial repair and avoidance of atherosclerotic plaque formation. Following a myocardial infarction, neoagiogenesis occurs after the "hot" phase of the inflammatory process has subsided (Day 5) when VEGF levels peak (Day 7) and then gradually subside to baseline (Days 14-21). During this phase of the healing process, endothelial precursors are mobilized and recruited to the infarct site. The chemokine stromal cell derived factor-1 (SDF-1), also plays a role in cell homing to areas of ischemic damage. SDF-1 gene expression is up-regulated during hypoxia, by hypoxia inducible factor-1. Up-regulation is proportionate to the degree of tissue hypoxia thus creating a gradient of SDF-1. SDF-1 is the ligand for the CXCR-4 receptor, which is expressed by CD34+ cells. These cells are capable of homing to areas of ischemia, rich in SDF-1, including infarcted myocardium. Virtually all CD34+ CXCR-4+ cells co-express VEGFR-2 and therefore migrate in response to VEGF as well as SDF-1. CD34+CXCR-4+ VEGF-2 cells, once recruited are capable of contributing to neoangiogenesis.

In the usual infarct setting, however, neoangiogenesis is unable to support the increased demands posed by compensatory myocardial hypertrophy. As a result there is the common occurrence of infarct extension and fibrous replacement, regardless of large vessel revascularization and appropriate medical management of ventricular wall stresses. Thus, intense interest has developed in evaluating the ability of precursors of endothelial and myocardial cells to limit damage to the myocardium after infarction and limit or prevent ventricular remodeling.

To significantly increase the circulating frequency of hematopoietic precursors, recombinant hematopoietic growth factors (rhG-CSF with or without rhSCF) have been administered to animals induced to have myocardial infarctions by coronary artery ligation. Orlic and colleagues demonstrated increased cardiac wall thickness and improved cardiac function in an infarction model in mice treated daily with hematopoietic growth factors subcutaneously (rat SCF and recombinant human G-CSF) starting 5 days before induced myocardial infarction and continuing for three days post (30).

However, this same group reported an adverse outcome among primates treated identically with hematopoietic growth factors. Rhesus monkeys received hematopoietic growth factor(s) (G-CSF w/w.o. SCF) for 5 days. Growth factor was started before the induced infarction and continued for the first three days (post infarct) of the "hot" phase of the inflammatory healing process (46). Treated animals had no evidence of infarct zone regeneration, had a greater incidence of mortality when treated with combined growth factors, and evidence to suggest a trend toward worse global cardiac function when compared to untreated controls. The authors postulate that the hematopoietic growth factors caused a significant increase in neutrophil count and reactivity, which is a known poor prognostic feature during the first five days of the post-infarct ("hot" phase) period. SCF, in addition to further increasing neutrophil counts and activity when added to G-CSF may also have intensified infarct zone inflammation, presumably due to recruitment of more neutrophils to the infarct site and intensifying the early (deleterious) inflammatory cytokine cascade.

Finally, Kang et al. experienced an un-expectantly high rate of in-stent re-stenosis among patients given G-CSF to mobilize blood stem cells soon after myocardial infarction. Thus, the use of hematopoietic growth factors particularly in the early post infarct setting (hot phase) is not ideal.

There is a need in the field of new technology to address heart failure, especially for suppression of inflammation after myocardial infarct.

SUMMARY

Embodiment 1 involves a method of preventing, and/or inhibiting, and/or reversing heart failure, and/or post infarct pathological remodeling comprising the steps of: a) identifying a patient suffering from heart failure and/or a patient having undergoing a myocardial infact; b) extracting from said patient immune cells; c) contacting said immune cells with regenerative cells in a manner so that regenerative cells endow onto said immune cells properties capable of inhibiting and/or reversing heart failure; and d) administering said immune cells into said patient.

2. The method of embodiment 1, wherein said heart failure is associated with myocardial damage.

3. The method of embodiment 1, wherein said heart failure is associated with alcoholism.

4. The method of embodiment 1, wherein said heart failure is associated with viral damage.

5. The method of embodiment 1, wherein said heart failure is associated with inflammation.

6. The method of embodiment 1, wherein said heart failure occurs as a result of a myocardial infarct 7. The method of embodiment 1, wherein said heart failure is autoimmune mediated.

8. The method of embodiment 1, wherein said immune cells are extracted from a patient who is not the recipient.

9. The method of embodiment 8, wherein said immune cells are xenogeneic.

10. The method of embodiment 8, wherein said immune cells are cord blood derived.

11. The method of embodiment 8, wherein said immune cells are derived from pluripotent stem cells.

12. The method of embodiment 1, wherein said immune cells are cultured together with said regenerative cells in the presence of an activator of an immune receptor.

13. The method of embodiment 12, wherein said immune receptor activates immunotyrosine activation motifs.

14. The method of embodiment 12, wherein said immune receptor activates NF-AT.

15. The method of embodiment 12, wherein said immune receptor activates NF-kappa B.

16. The method of embodiment 12, wherein said immune receptor activates STAT-3.

16. The method of embodiment 12, wherein said immune receptor activates STAT-4.

17. The method of embodiment 12, wherein said immune receptor activates janus activated kinase.

18. The method of embodiment 12, wherein said immune receptor activates MAP-kinase.

19. The method of embodiment 12, wherein said immune receptor is TLR. 1

20. The method of embodiment 19, wherein said TLR-1 is activated by Pam3CSK4.

21. The method of embodiment 12, wherein said immune receptor is TLR-2

22. The method of embodiment 20, wherein said TLR-2 is activated by HKLM.

23. The method of embodiment 12, wherein said immune receptor is TLR-3.

24. The method of embodiment 23, wherein said TLR-3 is activated by Poly:IC.

25. The method of embodiment 12, wherein said immune receptor is TLR-4.

26. The method of embodiment 25, wherein said TLR-4 is activated by LPS.

27. The method of embodiment 25, wherein said TLR-4 is activated by Buprenorphine.

28. The method of embodiment 25, wherein said TLR-4 is activated by Carbamazepine.

29. The method of embodiment 25, wherein said TLR-4 is activated by Fentanyl.

30. The method of embodiment 25, wherein said TLR-4 is activated by Levorphanol.

31. The method of embodiment 25, wherein said TLR-4 is activated by Methadone.

32. The method of embodiment 25, wherein said TLR-4 is activated by Cocaine.

33. The method of embodiment 25, wherein said TLR-4 is activated by Morphine.

34. The method of embodiment 25, wherein said TLR-4 is activated by Oxcarbazepine.

35. The method of embodiment 25, wherein said TLR-4 is activated by Oxycodone.

36. The method of embodiment 25, wherein said TLR-4 is activated by Pethidine.

37. The method of embodiment 25, wherein said TLR-4 is activated by Glucuronoxylomannan from *Cryptococcus*.

36. The method of embodiment 25, wherein said TLR-4 is activated by Morphine-3-glucuronide.

37. The method of embodiment 25, wherein said TLR-4 is activated by lipoteichoic acid.

38. The method of embodiment 25, wherein said TLR-4 is activated by beta.-defensin 2.

39. The method of embodiment 25, wherein said TLR-4 is activated by low molecular weight hyaluronic acid.

40. The method of embodiment 39, wherein said low molecular weight hyaluronic acid has a molecular weight of <1000 kDa.

41. The method of embodiment 39, wherein said low molecular weight hyaluronic acid has a molecular weight of <500 kDa.

42. The method of embodiment 39, wherein said low molecular weight hyaluronic acid has a molecular weight of <250 kDa.

43. The method of embodiment 39, wherein said low molecular weight hyaluronic acid has a molecular weight of <100 kDa.

44. The method of embodiment 25, wherein said TLR-4 is activated by fibronectin EDA.

45. The method of embodiment 25, wherein said TLR-4 is activated by snapin.

46. The method of embodiment 25, wherein said TLR-4 is activated by tenascin C.

47. The method of embodiment 12, wherein said immune receptor is TLR-5.

48. The method of embodiment 47, wherein said TLR-5 is activated by flaggelin.

49. The method of embodiment 12, wherein said immune receptor is TLR-6.

50. The method of embodiment 49, wherein said TLR-6 is activated by FSL-1.

51. The method of embodiment 12, wherein said immune receptor is TLR-7.

52. The method of embodiment 51, wherein said TLR-7 is activated by imiquimod.

53. The method of embodiment 12, wherein said immune receptor is TLR-8.

54. The method of embodiment 53, wherein said TLR-8 is activated by ssRNA40/LyoVec.

55. The method of embodiment 12, wherein said immune receptor is TLR-9.

56. The method of embodiment 55, wherein said TLR-9 is activated by a CpG oligonucleotide.

57. The method of embodiment 55, wherein said TLR-9 is activated by ODN2006.

58. The method of embodiment 55, wherein said TLR-9 is activated by Agatolimod.

59. The method of embodiment 55, wherein said TLR-9 is activated by ODN2007.

60. The method of embodiment 55, wherein said TLR-9 is activated by ODN1668.

61. The method of embodiment 55, wherein said TLR-9 is activated by ODN1826.
62. The method of embodiment 55, wherein said TLR-9 is activated by ODN BW006.
63. The method of embodiment 55, wherein said TLR-9 is activated by ODN D SL01.
64. The method of embodiment 55, wherein said TLR-9 is activated by ODN 2395.
65. The method of embodiment 55, wherein said TLR-9 is activated by ODN M362.
66. The method of embodiment 55, wherein said TLR-9 is activated by ODN SL03.
67. The method of embodiment 1, wherein said regenerative cell is a stem cell.
68. The method of embodiment 67, wherein said stem cell is a hematopoietic stem cell.
69. The method of embodiment 68, wherein said hematopoietic stem cell is capable of generating leukocytic, lymphocytic, thrombocytic and erythrocytic cells when transplanted into an immunodeficient animal.
70. The method of embodiment 69, wherein said hematopoietic stem cell expresses interleukin-3 receptor.
71. The method of embodiment 69, wherein said hematopoietic stem cell expresses interleukin-1 receptor.
72. The method of embodiment 69, wherein said hematopoietic stem cell expresses c-met.
73. The method of embodiment 69, wherein said hematopoietic stem cell expresses mpl.
74. The method of embodiment 69, wherein said hematopoietic stem cell expresses interleukin-11 receptor.
75. The method of embodiment 69, wherein said hematopoietic stem cell expresses G-CSF receptor.
76. The method of embodiment 69, wherein said hematopoietic stem cell expresses GM-CSF receptor.
77. The method of embodiment 69, wherein said hematopoietic stem cell expresses M-CSF receptor.
78. The method of embodiment 69, wherein said hematopoietic stem cell expresses VEGF-receptor.
79. The method of embodiment 69, wherein said hematopoietic stem cell expresses c-kit.
80. The method of embodiment 69, wherein said hematopoietic stem cell expresses CD33.
81. The method of embodiment 69, wherein said hematopoietic stem cell expresses CD133.
82. The method of embodiment 69, wherein said hematopoietic stem cell expresses CD34.
83. The method of embodiment 69, wherein said hematopoietic stem cell expresses Fas ligand.
84. The method of embodiment 69, wherein said hematopoietic stem cell does not express lineage markers.
85. The method of embodiment 69, wherein said hematopoietic stem cell does not express CD14.
86. The method of embodiment 69, wherein said hematopoietic stem cell does not express CD16.
87. The method of embodiment 69, wherein said hematopoietic stem cell does not express CD3.
88. The method of embodiment 69, wherein said hematopoietic stem cell does not express CD56.
89. The method of embodiment 69, wherein said hematopoietic stem cell does not express CD38.
90. The method of embodiment 69, wherein said hematopoietic stem cell does not express CD30.
91. The method of embodiment 1, wherein said regenerative cell is a mesenchymal stem cell.
92. The method of embodiment 91, wherein said mesenchymal stem cells are naturally occurring mesenchymal stem cells.
93. The method of embodiment 91, wherein said mesenchymal stem cells are generated in vitro.
94. The method of embodiment 92, wherein said naturally occurring mesenchymal stem cells are tissue derived.
95. The method of embodiment 92, wherein said naturally occurring mesenchymal stem cells are derived from a bodily fluid.
96. The method of embodiment 94, wherein said tissue derived mesenchymal stem cells are selected from a group comprising of: a) bone marrow; b) perivascular tissue; c) adipose tissue; d) placental tissue; e) amniotic membrane; f) omentum; g) tooth; h) umbilical cord tissue; i) fallopian tube tissue; j) hepatic tissue; k) renal tissue; l) cardiac tissue; m) tonsillar tissue; n) testicular tissue; o) ovarian tissue; p) neuronal tissue; q) auricular tissue; r) colonic tissue; s) submucosal tissue; t) hair follicle tissue; u) pancreatic tissue; v) skeletal muscle tissue; and w) subepithelial umbilical cord tissue.
97. The method of embodiment 94, wherein said tissue derived mesenchymal stem cells are isolated from tissues containing cells selected from a group of cells comprising of: endothelial cells, epithelial cells, dermal cells, endodermal cells, mesodermal cells, fibroblasts, osteocytes, chondrocytes, natural killer cells, dendritic cells, hepatic cells, pancreatic cells, stromal cells, salivary gland mucous cells, salivary gland serous cells, von Ebner's gland cells, mammary gland cells, lacrimal gland cells, ceruminous gland cells, eccrine sweat gland dark cells, eccrine sweat gland clear cells, apocrine sweat gland cells, gland of Moll cells, sebaceous gland cells. bowman's gland cells, Brunner's gland cells, seminal vesicle cells, prostate gland cells, bulbourethral gland cells, Bartholin's gland cells, gland of Littre cells, uterus endometrium cells, isolated goblet cells, stomach lining mucous cells, gastric gland zymogenic cells, gastric gland oxyntic cells, pancreatic acinar cells, paneth cells, type II pneumocytes, clara cells, somatotropes, lactotropes, thyrotropes, gonadotropes, corticotropes, intermediate pituitary cells, magnocellular neurosecretory cells, gut cells, respiratory tract cells, thyroid epithelial cells, parafollicular cells, parathyroid gland cells, parathyroid chief cell, oxyphil cell, adrenal gland cells, chromaffin cells, Leydig cells, theca interna cells, corpus luteum cells, granulosa lutein cells, theca lutein cells, juxtaglomerular cell, macula densa cells, peripolar cells, mesangial cell, blood vessel and lymphatic vascular endothelial fenestrated cells, blood vessel and lymphatic vascular endothelial continuous cells, blood vessel and lymphatic vascular endothelial splenic cells, synovial cells, serosal cell (lining peritoneal, pleural, and pericardial cavities), squamous cells, columnar cells, dark cells, vestibular membrane cell (lining endolymphatic space of ear), stria vascularis basal cells, stria vascularis marginal cell (lining endolymphatic space of ear), cells of Claudius, cells of Boettcher, choroid plexus cells, pia-arachnoid squamous cells, pigmented ciliary epithelium cells, nonpigmented ciliary epithelium cells, corneal endothelial cells, peg cells, respiratory tract ciliated cells, oviduct ciliated cell, uterine endometrial ciliated cells, rete testis ciliated cells, ductulus efferens ciliated cells, ciliated ependymal cells, epidermal keratinocytes, epidermal basal cells, keratinocyte of fingernails and toenails, nail bed basal cells, medullary hair shaft cells, cortical hair shaft cells, cuticular hair shaft cells, cuticular hair root sheath cells, hair root sheath cells of Huxley's layer, hair root sheath cells of Henle's layer, external hair root sheath cells, hair matrix cells, surface epithelial cells of stratified squamous epithelium, basal cell of epithelia, urinary epithelium cells, auditory inner hair cells of organ of *Corti*, auditory outer hair cells of organ of Corti, basal cells of olfactory epithelium, cold-sensitive primary sensory neurons, heat-sensitive primary sensory neurons, Merkel cells of epidermis, olfactory receptor neurons, pain-sensitive primary sensory neurons, photoreceptor rod cells, photoreceptor blue-sensitive cone cells, photoreceptor green-sensitive cone cells, photoreceptor red-sensitive cone cells, proprioceptive primary sensory neurons, touch-sensitive primary sensory neurons, type I carotid body cells, type II carotid body cell (blood pH sensor), type I hair cell of vestibular apparatus of ear (acceleration and gravity), type II hair cells of vestibular apparatus of ear, type I taste bud cells cholinergic neural cells, adrenergic neural cells, peptidergic neural cells, inner pillar cells of organ of Corti, outer pillar cells of organ of Corti, inner phalangeal cells of organ of Corti, outer phalangeal cells of organ of Corti, border cells of organ of Corti, Hensen cells of organ of Corti, vestibular apparatus supporting cells, taste bud supporting cells, olfactory epithelium supporting cells, Schwann cells, satellite cells, enteric glial cells, astrocytes, neurons, oligodendrocytes, spindle neurons, anterior lens epithelial cells, crystallin-containing lens fiber cells, hepatocytes, adipocytes, white fat cells, brown fat cells, liver lipocytes, kidney glomerulus parietal cells, kidney glomerulus podocytes, kidney proximal tubule brush border cells, loop of Henle thin segment cells, kidney distal tubule cells, kidney collecting duct cells, type I pneumocytes, pancreatic duct cells, nonstriated duct cells, duct cells, intestinal brush border cells, exocrine gland striated duct cells, gall bladder epithelial cells, ductulus efferens nonciliated cells, epididymal principal cells, epididymal basal cells, ameloblast epithelial cells, planum semilunatum epithelial cells, organ of Corti interdental epithelial cells, loose connective tissue fibroblasts, corneal keratocytes, tendon fibroblasts, bone marrow reticular tissue fibroblasts, nonepithelial fibroblasts, pericytes, nucleus pulposus cells, cementoblast/cementocytes, odontoblasts, odontocytes, hyaline cartilage chondrocytes, fibrocartilage chondrocytes, elastic cartilage chondrocytes, osteoblasts, osteocytes, osteoclasts, osteoprogenitor cells, hyalocytes, stellate cells (ear), hepatic stellate cells (Ito cells), pancreatic stelle cells, red skeletal muscle cells, white skeletal muscle cells, intermediate skeletal muscle cells, nuclear bag cells of muscle spindle, nuclear chain cells of muscle spindle, satellite cells, ordinary heart muscle cells, nodal heart muscle cells, Purkinje fiber cells, smooth muscle cells, myoepithelial cells of iris, myoepithelial cell of exocrine glands, melanocytes, retinal pigmented epithelial cells, oogonia/oocytes, spermatids, spermatocytes, spermatogonium cells, spermatozoa, ovarian follicle cells, Sertoli cells, thymus epithelial cell, and/or interstitial kidney cells.

98. The method of embodiment 91, wherein said mesenchymal stem cells are plastic adherent.

99. The method of embodiment 91, wherein said mesenchymal stem cells express a marker selected from a group comprising of: a) CD73; b) CD90; and c) CD105.

100. The method of embodiment 91, wherein said mesenchymal stem cells lack expression of a marker selected from a group comprising of: a) CD14; b) CD45; and c) CD34.

101. The method of embodiment 96, wherein said mesenchymal stem cells from umbilical cord tissue express markers selected from a group comprising of; a) oxidized low density lipoprotein receptor 1, b) chemokine receptor ligand 3; and c) granulocyte chemotactic protein.

102. The method of embodiment 96, wherein said mesenchymal stem cells from umbilical cord tissue do not express markers selected from a group comprising of: a) CD117; b) CD31; c) CD34; and CD45;

103. The method of embodiment 96, wherein said mesenchymal stem cells from umbilical cord tissue express, relative to a human fibroblast, increased levels of interleukin 8 and reticulon 1

104. The method of embodiment 96, wherein said mesenchymal stem cells from umbilical cord tissue have the potential to differentiate into cells of at least a skeletal muscle, vascular smooth muscle, pericyte or vascular endothelium phenotype.

105. The method of embodiment 96, wherein said mesenchymal stem cells from umbilical cord tissue express markers selected from a group comprising of: a) CD10; b) CD13; c) CD44; d) CD73; and e) CD90.

106. The method of embodiment 96, wherein said umbilical cord tissue mesenchymal stem cell is an isolated umbilical cord tissue cell isolated from umbilical cord tissue substantially free of blood that is capable of self-renewal and expansion in culture, 107. The method of embodiment 106, wherein said umbilical cord tissue mesenchymal stem cells has the potential to differentiate into cells of other phenotypes.

108. The method of embodiment 107, wherein said other phenotypes comprise: a) osteocytic; b) adipogenic; and c) chondrogenic differentiation.

109. The method of embodiment 96, wherein said cord tissue derived mesenchymal stem cells can undergo at least 20 doublings in culture.

100. The method of embodiment 96, wherein said cord tissue derived mesenchymal stem cell maintains a normal karyotype upon passaging 111. The method of embodiment 96, wherein said cord tissue derived mesenchymal stem cell expresses a marker selected from a group of markers comprised of: a) CD10 b) CD13; c) CD44; d) CD73; e) CD90; f) PDGFr-alpha; g) PD-L2; and h) HLA-A,B,C 112. The method of embodiment 96, wherein said cord tissue mesenchymal stem cells does not express one or more markers selected from a group comprising of; a) CD31; b) CD34; c) CD45; d) CD80; e) CD86; f) CD117; g) CD141; h) CD178; i) B7-H2; j) HLA-G and k) HLA-DR,DP,DQ.

113. The method of embodiment 96, wherein said umbilical cord tissue-derived cell secretes factors selected from a group comprising of: a) MCP-1; b) MIP1beta; c) IL-6; d) IL-8; e) GCP-2; f) HGF; g) KGF; h) FGF; i) HB-EGF; j) BDNF; k) TPO; 1) RANTES; and m) TIMP1

114. The method of embodiment 96, wherein said umbilical cord tissue derived cells express markers selected from a group comprising of: a) TRA1-60; b) TRA1-81; c) SSEA3; d) SSEA4; and e) NANOG.

115. The method of embodiment 96, wherein said umbilical cord tissue-derived cells are positive for alkaline phosphatase staining.

116. The method of embodiment 96, wherein said umbilical cord tissue-derived cells are capable of differentiating into one or more lineages selected from a group comprising of; a) ectoderm; b) mesoderm, and; c) endoderm.

117. The method of embodiment 96, wherein said bone marrow derived mesenchymal stem cells possess markers selected from a group comprising of: a) CD73; b) CD90; and c) CD105.

118. The method of embodiment 96, wherein said bone marrow derived mesenchymal stem cells possess markers selected from a group comprising of: a) LFA-3; b) ICAM-1; c) PECAM-1; d) P-selectin; e) L-selectin; f) CD49b/CD29; g) CD49c/CD29; h) CD49d/CD29; i) CD29; j) CD18; k) CD61; 1) 6-19; m) thrombomodulin; n) telomerase; o) CD10; p) CD13; and q) integrin beta.

119. The method of embodiment 96, wherein said bone marrow derived mesenchymal stem cell is a mesenchymal stem cell progenitor cell.
120. The method of embodiment 119, wherein said mesenchymal progenitor cells are a population of bone marrow mesenchymal stem cells enriched for cells containing STRO-1
121. The method of embodiment 120, wherein said mesenchymal progenitor cells express both STRO-1 and VCAM-1.
122. A method of embodiment 120, wherein said STRO-1 expressing cells are negative for at least one marker selected from the group consisting of: a) CBFA-1; b) collagen type II; c) PPAR.gamma2; d) osteopontin; e) osteocalcin; f) parathyroid hormone receptor; g) leptin; h) H-ALBP; i) aggrecan; j) Ki67, and k) glycophorin A.
123. The method of embodiment 96, wherein said bone marrow mesenchymal stem cells lack expression of CD14, CD34, and CD45.
124. The method of embodiment 122, wherein said STRO-1 expressing cells are positive for a marker selected from a group comprising of: a) VACM-1; b) TKY-1; c) CD146 and; d) STRO-2
125. The method of embodiment 96, wherein said bone marrow mesenchymal stem cell express markers selected from a group comprising of: a) CD13; b) CD34; c) CD56 and; d) CD117
126. The method of embodiment 125, wherein said bone marrow mesenchymal stem cells do not express CD10.
127. The method of embodiment 125, wherein said bone marrow mesenchymal stem cells do not express CD2, CD5, CD14, CD19, CD33, CD45, and DRII.
128. The method of embodiment 125, wherein said bone marrow mesenchymal stem cells express CD13, CD34, CD56, CD90, CD117 and nestin, and which do not express CD2, CD3, CD10, CD14, CD16, CD31, CD33, CD45 and CD64.
129. The method of embodiment 96, wherein said skeletal muscle stem cells express markers selected from a group comprising of: a) CD13; b) CD34; c) CD56 and; d) CD117
130. The method of embodiment 129, wherein said skeletal muscle mesenchymal stem cells do not express CD10.
131. The method of embodiment 129, wherein said skeletal muscle mesenchymal stem cells do not express CD2, CD5, CD14, CD19, CD33, CD45, and DRII.
132. The method of embodiment 129, wherein said bone marrow mesenchymal stem cells express CD13, CD34, CD56, CD90, CD117 and nestin, and which do not express CD2, CD3, CD10, CD14, CD16, CD31, CD33, CD45 and CD64.
133. The method of embodiment 96, wherein said subepithelial umbilical cord derived mesenchymal stem cells possess markers selected from a group comprising of; a) CD29; b) CD73; c) CD90; d) CD166; e) SSEA4; f) CD9; g) CD44; h) CD146; and i) CD105
134. The method of embodiment 133, wherein said subepithelial umbilical cord derived mesenchymal stem cells do not express markers selected from a group comprising of; a) CD45; b) CD34; c) CD14; d) CD79; e) CD106; f) CD86; g) CD80; h) CD19; i) CD117; j) Stro-1 and k) HLA-DR.
135. The method of embodiment 133, wherein said subepithelial umbilical cord derived mesenchymal stem cells express CD29, CD73, CD90, CD166, SSEA4, CD9, CD44, CD146, and CD105.
136. The method of embodiment 133, wherein said subepithelial umbilical cord derived mesenchymal stem cells do not express CD45, CD34, CD14, CD79, CD106, CD86, CD80, CD19, CD117, Stro-1, and HLA-DR.
137. The method of embodiment 133, wherein said subepithelial umbilical cord derived mesenchymal stem cells are positive for SOX2.
138. The method of embodiment 133, wherein said subepithelial umbilical cord derived mesenchymal stem cells are positive for OCT4.
139. The method of embodiment 133, wherein said subepithelial umbilical cord derived mesenchymal stem cells are positive for OCT4 and SOX2.
140. The method of embodiment 1, wherein said immune cells are T cells.
141. The method of embodiment 140, wherein said T cells are CD4 cells.
142. The method of embodiment 140, wherein said T cells are CD8 cells.
143. The method of embodiment 140, wherein said T cells are NKT cells.
144. The method of embodiment 140, wherein said T cells are gamma delta T cells.
145. The method of embodiment 140, wherein said T cells are Th1 cells.
146. The method of embodiment 145, wherein said Th1 cells have a propensity for producing interferon gamma over interleukin 4 upon stimulation via the CD3 protein.
147. The method of embodiment 145, wherein said Th1 cells express STAT4.
148. The method of embodiment 145, wherein said Th1 cells express STAT1.
149. The method of embodiment 145, wherein said Th1 cells express T-bet.
150. The method of embodiment 145, wherein said Th1 cells express CCR1.
151. The method of embodiment 145, wherein said Th1 cells express CCR5.
152. The method of embodiment 145, wherein said Th1 cells express CXCR3.
153. The method of embodiment 145, wherein said Th1 cells express CD119.
154. The method of embodiment 145, wherein said Th1 cells express interferon gamma receptor II.
155. The method of embodiment 145, wherein said Th1 cells express IL-18 receptor.
156. The method of embodiment 145, wherein said Th1 cells express IL-12 receptor.
157. The method of embodiment 145, wherein said Th1 cells express IL-27 receptor.
158. The method of embodiment 140, wherein said T cells are Th2 cells.
159. The method of embodiment 158, wherein said Th2 cells have a proclivity to produce more interleukin-4 than interferon gamma upon stimulation via CD3.
160. The method of embodiment 158, wherein said Th2 cells express GATA-3.
161. The method of embodiment 158, wherein said Th2 cells express IRF-4.
162. The method of embodiment 158, wherein said Th2 cells express STAT5.
163. The method of embodiment 158, wherein said Th2 cells express STAT6.
164. The method of embodiment 158, wherein said Th2 cells express CCR3.
165. The method of embodiment 158, wherein said Th2 cells express CCR4.
166. The method of embodiment 158, wherein said Th2 cells express CCR8.

167. The method of embodiment 158, wherein said Th2 cells express CXCR4.
168. The method of embodiment 158, wherein said Th2 cells express interleukin-4 receptor.
169. The method of embodiment 158, wherein said Th2 cells express interleukin-33 receptor.
170. The method of embodiment 140, wherein said T cells are Th9 cells.
171. The method of embodiment 170, wherein said Th9 cell produces interleukin-9.
172. The method of embodiment 170, wherein said Th9 cell expresses IRF4.
173. The method of embodiment 170, wherein said Th9 cell expresses PU.1.
174. The method of embodiment 170, wherein said Th9 cell secretes CCL17.
175. The method of embodiment 170, wherein said Th9 cell secretes CCL22.
176. The method of embodiment 170, wherein said Th9 cell secretes IL-10.
177. The method of embodiment 170, wherein said Th9 cell expresses TGF-beta receptor II.
178. The method of embodiment 140, wherein said T cell is a follicular helper T cell.
179. The method of embodiment 178, wherein said follicular helper T cell expresses bcl-6.
180. The method of embodiment 178, wherein said follicular helper T cell expresses c-maf.
181. The method of embodiment 178, wherein said follicular helper T cell expresses stat-3.
182. The method of embodiment 178, wherein said follicular helper T cell secretes CXCL-13.
183. The method of embodiment 178, wherein said follicular helper T cell secretes interferon gamma.
184. The method of embodiment 178, wherein said follicular helper T cell secretes interleukin-4.
185. The method of embodiment 178, wherein said follicular helper T cell secretes IL-10.
186. The method of embodiment 178, wherein said follicular helper T cell secretes IL-17A.
187. The method of embodiment 178, wherein said follicular helper T cell secretes IL-17F.
188. The method of embodiment 178, wherein said follicular helper T cell secretes IL-21.
189. The method of embodiment 178, wherein said follicular helper T cell expresses BTLA-4.
190. The method of embodiment 178, wherein said follicular helper T cell secretes CD40 ligand.
191. The method of embodiment 178, wherein said follicular helper T cell expresses CD57.
192. The method of embodiment 178, wherein said follicular helper T cell expresses CD84.
193. The method of embodiment 178, wherein said follicular helper T cell expresses CXCR-4.
194. The method of embodiment 178, wherein said follicular helper T cell expresses CXCR-5.
195. The method of embodiment 178, wherein said follicular helper T cell expresses ICOS.
196. The method of embodiment 178, wherein said follicular helper T cell expresses IL-6 receptor.
197. The method of embodiment 178, wherein said follicular helper T cell expresses IL-21 receptor.
198. The method of embodiment 178, wherein said follicular helper T cell expresses CD10.
199. The method of embodiment 178, wherein said follicular helper T cell expresses OX40.
200. The method of embodiment 178, wherein said follicular helper T cell expresses PD-1.
201. The method of embodiment 178, wherein said follicular helper T cell expresses CD150.
202. The method of embodiment 140, wherein said T cell is a Th17 cell.
203. The method of embodiment 202, wherein said Th17 cell secretes interleukin-17A.
204. The method of embodiment 202, wherein said Th17 cell secretes interleukin-17F.
205. The method of embodiment 202, wherein said Th17 cell secretes IL-21.
206. The method of embodiment 202, wherein said Th17 cell secretes IL-26.
207. The method of embodiment 202, wherein said Th17 cell secretes CCL20.
208. The method of embodiment 202, wherein said Th17 cell expresses BATF.
209. The method of embodiment 202, wherein said Th17 cell expresses IRF4.
210. The method of embodiment 202, wherein said Th17 cell expresses ROR alpha.
211. The method of embodiment 202, wherein said Th17 cell expresses ROR gamma.
212. The method of embodiment 202, wherein said Th17 cell expresses STAT5.
213. The method of embodiment 202, wherein said Th17 cell expresses CCR4.
214. The method of embodiment 202, wherein said Th17 cell expresses CCR6.
215. The method of embodiment 202, wherein said Th17 cell expresses IL-1 receptor.
216. The method of embodiment 202, wherein said Th17 cell expresses IL-6 receptor alpha.
217. The method of embodiment 202, wherein said Th17 cell expresses IL-21 receptor.
218. The method of embodiment 202, wherein said Th17 cell expresses IL-23 receptor.
219. The method of embodiment 140, wherein said T cell is a Th22 cell.
220. The method of embodiment 219, wherein said Th22 cell secretes IL-10.
221. The method of embodiment 219, wherein said Th22 cell secretes IL-13.
222. The method of embodiment 219, wherein said Th22 cell secretes FGF-1.
223. The method of embodiment 219, wherein said Th22 cell secretes FGF-2.
224. The method of embodiment 219, wherein said Th22 cell secretes FGF-5.
225. The method of embodiment 219, wherein said Th22 cell secretes IL-21.
226. The method of embodiment 219, wherein said Th22 cell secretes IL-22.
227. The method of embodiment 219, wherein said Th22 cell expresses AHR.
228. The method of embodiment 219, wherein said Th22 cell expresses batf.
229. The method of embodiment 219, wherein said Th22 cell expresses STAT-3
230. The method of embodiment 219, wherein said Th22 cell expresses CCR4.
231. The method of embodiment 219, wherein said Th22 cell expresses CCR6.
232. The method of embodiment 219, wherein said Th22 cell expresses CCR10.

233. The method of embodiment 219, wherein said Th22 cell expresses IL-6 receptor.

234. The method of embodiment 219, wherein said Th22 cell expresses TGF-beta receptor II.

235. The method of embodiment 219, wherein said Th22 cell expresses TNF receptor 1.

236. The method of embodiment 140, wherein said T cell is a T regulatory cell.

237. The method of embodiment 236, wherein said T regulatory cell expresses foxp-3.

238. The method of embodiment 236, wherein said T regulatory cell expresses Helios.

239. The method of embodiment 236, wherein said T regulatory cell expresses STAT5.

240. The method of embodiment 236, wherein said T regulatory cell expresses CD5.

241. The method of embodiment 236, wherein said T regulatory cell expresses CD25.

242. The method of embodiment 236, wherein said T regulatory cell expresses CD39.

243. The method of embodiment 236, wherein said T regulatory cell expresses CD105.

244. The method of embodiment 236, wherein said T regulatory cell expresses IL-7 receptor.

245. The method of embodiment 236, wherein said T regulatory cell expresses CTLA-4.

246. The method of embodiment 236, wherein said T regulatory cell expresses folate receptor.

247. The method of embodiment 236, wherein said T regulatory cell expresses CD223

248. The method of embodiment 236, wherein said T regulatory cell expresses LAP.

249. The method of embodiment 236, wherein said T regulatory cell expresses GARP.

250. The method of embodiment 236, wherein said T regulatory cell expresses Neuropilin.

251. The method of embodiment 236, wherein said T regulatory cell expresses CD134.

252. The method of embodiment 236, wherein said T regulatory cell expresses CD62 ligand.

253. The method of embodiment 236, wherein said T regulatory cell secretes IL-10.

254. The method of embodiment 236, wherein said T regulatory cell secretes TGF-alpha.

255. The method of embodiment 236, wherein said T regulatory cell secretes TGF-beta.

256. The method of embodiment 236, wherein said T regulatory cell secretes soluble TNF receptor p55.

257. The method of embodiment 236, wherein said T regulatory cell secretes soluble TNF receptor p75.

258. The method of embodiment 236, wherein said T regulatory cell secretes IL-2.

259. The method of embodiment 236, wherein said T regulatory cell secretes soluble HLA-G.

260. The method of embodiment 236, wherein said T regulatory cell secretes soluble Fas ligand.

261. The method of embodiment 236, wherein said T regulatory cell secretes IL-35.

262. The method of embodiment 236, wherein said T regulatory cell secretes VEGF.

263. The method of embodiment 236, wherein said T regulatory cell secretes HGF.

264. The method of embodiment 236, wherein said T regulatory cell secretes FGF1.

265. The method of embodiment 236, wherein said T regulatory cell secretes FGF2.

266. The method of embodiment 236, wherein said T regulatory cell secretes FGF5.

267. The method of embodiment 236, wherein said T regulatory cell secretes Galectin 1.

268. The method of embodiment 236, wherein said T regulatory cell secretes Galectin 9.

269. The method of embodiment 236, wherein said T regulatory cell secretes IL-20.

270. The method of embodiment 236, wherein said T regulatory cell expresses perforin.

271. The method of embodiment 236, wherein said T regulatory cell expresses granzyme.

272. The method of embodiment 236, wherein said T regulatory cell inhibits activation of a conventional T cell.

273. The method of embodiment 272, wherein said conventional T cell does not express CD25.

274. The method of embodiment 272, wherein said conventional T cell is activated by ligation of CD3.

275. The method of embodiment 272, wherein said T conventional T cell is activated by ligation of CD3 and CD28.

276. The method of embodiment 272, wherein said activation of said conventional T cell is proliferation.

277. The method of embodiment 133, wherein said activation of said conventional T cell is cytokine secretion.

278. The method of embodiment 277, wherein said cytokine is IL-2.

279. The method of embodiment 277, wherein said cytokine is IL-4.

280. The method of embodiment 277, wherein said cytokine is IL-6.

281. The method of embodiment 277, wherein said cytokine is IL-10.

282. The method of embodiment 277, wherein said cytokine is IL-12.

283. The method of embodiment 277, wherein said cytokine is IL-7.

284. The method of embodiment 277, wherein said cytokine is IL-13.

285. The method of embodiment 277, wherein said cytokine is IL-15.

286. The method of embodiment 277, wherein said cytokine is IL-18.

287. The method of embodiment 1, wherein said immune cells are peripheral blood mononuclear cells.

288. The method of embodiment 287, wherein said peripheral blood mononuclear cells are treated with an immune modulatory agent prior to contacting with said regenerative cells.

289. The method of embodiment 288, wherein said immune modulatory agent is ultraviolet light.

290. The method of embodiment 288, wherein said immune modulatory agent is HGF.

291. The method of embodiment 288, wherein said immune modulatory agent is oxytocin.

292. The method of embodiment 288, wherein said immune modulatory agent is NGF.

293. The method of embodiment 288, wherein said immune modulatory agent is FGF-1.

294. The method of embodiment 288, wherein said immune modulatory agent is FGF-2.

295. The method of embodiment 288, wherein said immune modulatory agent is a toll like receptor activator.

296. The method of embodiment 288, wherein oxytocin is administered to peripheral blood mononuclear cells in vitro for a period of 1 minute to 4 weeks.

297. The method of embodiment 286, wherein oxytocin is administered to peripheral blood mononuclear cells in vitro for a period of 2 hours to 1 week.
298. The method of embodiment 297, wherein oxytocin is administered to said fibroblasts in vitro for a period of 24 hours to 72 hours.
299. The method of embodiment 297, wherein said oxytocin is administered at a concentration of 10 nM-10 uM.
300. The method of embodiment 297, wherein said oxytocin is administered at a concentration of 100 nM-1 uM.
301. The method of embodiment 1, wherein an immune modulatory agent is administered to the combination of immune cells and regenerative cells.
302. The method of embodiment 301, wherein said immune modulatory agent is curcumin.
303. The method of embodiment 301, wherein said immune modulatory agent is TGF-beta.
304. The method of embodiment 301, wherein said immune modulatory agent is galectin-1.
305. The method of embodiment 301, wherein said immune modulatory agent is galectin-3.
306. The method of embodiment 301, wherein said immune modulatory agent is galectin-9.
307. The method of embodiment 301, wherein said immune modulatory agent is IL-1.
308. The method of embodiment 301, wherein said immune modulatory agent is IL-2.
309. The method of embodiment 301, wherein said immune modulatory agent is IL-4.
310. The method of embodiment 301, wherein said immune modulatory agent is IL-7.
311. The method of embodiment 301, wherein said immune modulatory agent is IL-10.
312. The method of embodiment 301, wherein said immune modulatory agent is IL-13.
313. The method of embodiment 301, wherein said immune modulatory agent is IL-15.
314. The method of embodiment 301, wherein said immune modulatory agent is IL-12.
315. The method of embodiment 301, wherein said immune modulatory agent is IL-18.
316. The method of embodiment 301, wherein said immune modulatory agent is IL-20.
317. The method of embodiment 301, wherein said immune modulatory agent is IL-22.
318. The method of embodiment 301, wherein said immune modulatory agent is IL-35.
319. A method of reducing cardiac damage after a myocardial infarct, said method comprising of; a) obtaining a patient who has underwent a myocardial infarct; b) extracting from said patient monocytes; c) culturing monocytes from said patient with a regenerative cell; d) priming said monocytes with cardiac antigens; e) generating a population of tolerogeneic dendritic cells from said monocytes, wherein said tolerogenic dendritic cells are pulsed with cardiac antigens and f) administering said cells into said patient who has underwent a myocardial infarct.
320. The method of embodiment 319, wherein said myocardial infarct is associated with release of myocardial antigens.

BRIEF DESCRIPTION OF THE DRAWINGS

FIG. 1 is a bar graph showing the effects of reprogrammed immune cells on survival rates of myocardial infarction induced mice.

DESCRIPTION OF THE INVENTION

For the practice of the invention, MSC are used to reprogramme immune cells in order to endow cardiac regenerative activity can be utilized as was previously performed in clinical trials with non-selected MSC. "Mesenchymal stem cell" or "MSC" in some embodiments refers to cells that are (1) adherent to plastic, (2) express CD73, CD90, and CD105 antigens, while being CD14, CD34, CD45, and HLA-DR negative, and (3) possess ability to differentiate to osteogenic, chondrogenic and adipogenic lineage. Other cells possessing mesenchymal-like properties are included within the definition of "mesenchymal stem cell", with the condition that said cells possess at least one of the following: a) regenerative activity; b) production of growth factors; c) ability to induce a healing response, either directly, or through elicitation of endogenous host repair mechanisms. As used herein, "mesenchymal stromal cell" or ore mesenchymal stem cell can be used interchangeably. Said MSC can be derived from any tissue including, but not limited to, bone marrow, adipose tissue, amniotic fluid, endometrium, trophoblast-derived tissues, cord blood, Wharton jelly, placenta, amniotic tissue, derived from pluripotent stem cells, and tooth. In some definitions of "MSC", said cells include cells that are CD34 positive upon initial isolation from tissue but are similar to cells described about phenotypically and functionally. As used herein, "MSC" may includes cells that are isolated from tissues using cell surface markers selected from the list comprised of NGF-R, PDGF-R, EGF-R, IGF-R, CD29, CD49a, CD56, CD63, CD73, CD105, CD106, CD140b, CD146, CD271, MSCA-1, SSEA4, STRO-1 and STRO-3 or any combination thereof, and satisfy the ISCT criteria either before or after expansion. Furthermore, as used herein, in some contexts, "MSC" includes cells described in the literature as bone marrow stromal stem cells (BMSSC), marrow-isolated adult multipotent inducible cells (MIAMI) cells, multipotent adult progenitor cells (MAPC), mesenchymal adult stem cells (MASCS), MultiStem®, Prochymal®, remestemcel-L, Mesenchymal Precursor Cells (MPCs), Dental Pulp Stem Cells (DPSCs), PLX cells, PLX-PAD, AlloStem®, Astrostem®, Ixmyelocel-T, MSC-NTF, NurOwn™, Stemedyne™-MSC, Stempeucel®, StempeucelCLI, StempeucelOA, HiQCell, Hearticellgram-AMI, Revascor®, Cardiorel®, Cartistem®, Pneumostem®, Promostem®, Homeo-GH, AC607, PDA001, SB623, CX601, AC607, Endometrial Regenerative Cells (ERC), adipose-derived stem and regenerative cells (ADRCs).

In some embodiments, dendritic cells are generated which possess tolerogenic activity and said dendritic cells are pulsed with cardiac antigens. Said cardiac antigens include the myosin heavy chain [1]. Said dendritic cells can be made tolerogenic by culture in cytokines such as IL-10 or they can be further made tolerogenic by culture with regenerative cells. In one embodiment said regenerative cells are mesenchymal stem cells. Generation of clinical grade dendritic cells is described in the following papers which are incorporated by reference [2-126].

Mesenchymal stem cells (MSCs) are adult stem cells with self-renewing abilities[127] and have been shown to differentiate into a wide range of tissues including mesoderm- and nonmesoderm-derived[127, 128], such as hepatocytes[129-134]. MSCs are capable of entering and maintaining satellite cell niches, particularly in hematopoiesis[135, 136], and are key in tissue repair and regeneration, aging, and regulating homeostasis[137-140]. In the case of heart failure, MSCs can aid in regeneration of cardiac tissue[141-147], and their interactions with the immune system[148-154] have potential as adjuvants during organ transplants[155], including cardiac transplantation[156].

MSCs were discovered in 1970 by Friedenstein et al[157] who demonstrated that bone marrow (BM) contained both hematopoietic stem cells (HSCs), which are non-plastic adherent, and a population of a more rare adherent cell. The adherent cells were able to form single cell colonies and were referred to as stromal cells. Those stromal cells, which are capable of self-renewal and expansion in culture are now referred to as mesenchymal stem cells (MSCs). Friedenstein was the first to show that MSCs could differentiate into mesoderm and to demonstrate their importance in controlling the hematopoietic niche [158].

In the 1980s, more research on MSCs found that they could differentiate into muscle, cartilage, bone and adipose-derived cells [159]. Caplan et al showed that MSCs are responsible for bone and cartilage regeneration induced by local cuing and genetic potential[160].

In the 1990s, Pittenger et al isolated MSCs from bone marrow and found that they retained their multilineage potential after expanding into selectively differentiated adipocytic, chondrocytic, or osteocytic lineages[128]. Likewise, Kopen et al showed that bone marrow MSCs differentiated into neural cells when exposed to the brain microenvironment[161]. In 1999, Petersen et al found that bone marrow-derived stem cells could be a source of hepatic oval cells in a rat model[162]. Specifically, they used male to female bone marrow transplant and subsequently induced blockade of hepatocyte proliferation by administration of a hepatotoxin followed by partial hepatectomy. As previously described, this procedure stimulates proliferation of LPC or "reserve cells" which generate new hepatocytes, such cells having previously identified as oval cells. Subsequent to the hepatectomy, Y chromosome, dipeptidyl peptidase IV enzyme, and L21-6 antigen were used to identify the newly generated oval cells, and their hepatocytic progeny to be of bone marrow origin.

The first decade of the 21' century saw a surge of research on MSCs, leading to a greater understanding of their nature and of the cellular process behind regeneration [127, 139, 140]. In 2005, Teratani et al identified growth factors allowing hepatic fate-specification in mice and showed that embryonic stem cells could differentiate into functional hepatocytes [163]. A unique property of MSC is their apparent hypoimmunogenicity and immune modulatory activity [164], which is present in MSC derived from various sources [165]. This is believed to account for the ability to achieve therapeutic effects in an allogeneic manner. Allogeneic bone marrow derived MSC have been used by academic investigators with clinical benefit treatment of diseases such as graft versus host (GVHD) [166-171], osteogenesis imperfecta [172], Hurler syndrome, metachromatic leukodystrophy [173], and acceleration of hematopoietic stem cell engraftment [174-176]. The company Athersys has successfully completed Phase I safety studies using allogeneic bone marrow MSCs is now in efficacy finding clinical trials (Phase II and Phase III) for Multiple Sclerosis, Crohn's Disease, and Graft Versus Host Disease using allogeneic bone marrow derived MSC. Intravenous administration of allogeneic MSCs by Osiris was also reported to induce a statistically significant improvement in cardiac function in a double-blind study [177].

Currently there several MSC-based therapies that have received governmental approvals including Prochymal™ which was registered in Canada and New Zealand for treatment of graft versus host disease [178, 179]. Although in terms of clinical translation bone marrow MSC are the most advanced, several other sources of MSC are known which possess various properties that may be useful for specific conditions. Bone marrow is also a source for hematopoietic stem cells (HSCs), which have also been used for cardiac regeneration. Likewise, human placenta is an easily accessible source of abundant MSCs, which can be differentiated in vitro. Finally, MSCs with tissue regenerative abilities can also be isolated from adipose tissue and induced to hepatocytes in large numbers.

In some embodiments of the invention reprogrammed immune cells are administered with MSC for treatment of heart failure. The discussion below provides examples of the use of MSC in heart failure, which may be useful for one of skill in the art to combine MSC with reprogrammed immune cells Methods of deriving cord tissue mesenchymal stem cells from human umbilical tissue are provided. The cells are capable of self-renewal and expansion in culture, and have the potential to differentiate into cells of other phenotypes. The method comprises (a) obtaining human umbilical tissue; (b) removing substantially all of blood to yield a substantially blood-free umbilical tissue, (c) dissociating the tissue by mechanical or enzymatic treatment, or both, (d) resuspending the tissue in a culture medium, and (e) providing growth conditions which allow for the growth of a human umbilicus-derived cell capable of self-renewal and expansion in culture and having the potential to differentiate into cells of other phenotypes. Tissue can be obtained from any completed pregnancy, term or less than term, whether delivered vaginally, or through other routes, for example surgical Cesarean section. Obtaining tissue from tissue banks is also considered within the scope of the present invention.

The tissue is rendered substantially free of blood by any means known in the art. For example, the blood can be physically removed by washing, rinsing, and diluting and the like, before or after bulk blood removal for example by suctioning or draining. Other means of obtaining a tissue substantially free of blood cells might include enzymatic or chemical treatment.

Dissociation of the umbilical tissues can be accomplished by any of the various techniques known in the art, including by mechanical disruption, for example, tissue can be aseptically cut with scissors, or a scalpel, or such tissue can be otherwise minced, blended, ground, or homogenized in any manner that is compatible with recovering intact or viable cells from human tissue.

In a presently preferred embodiment, the isolation procedure also utilizes an enzymatic digestion process. Many enzymes are known in the art to be useful for the isolation of individual cells from complex tissue matrices to facilitate growth in culture. As discussed above, a broad range of digestive enzymes for use in cell isolation from tissue is available to the skilled artisan. Ranging from weakly digestive (e.g. deoxyribonucleases and the neutral protease, dispase) to strongly digestive (e.g. papain and trypsin), such enzymes are available commercially. A nonexhaustive list of enzymes compatable herewith includes mucolytic enzyme activities, metalloproteases, neutral proteases, serine proteases (such as trypsin, chymotrypsin, or elastase), and deoxyribonucleases. Presently preferred are enzyme activities selected from metalloproteases, neutral proteases and mucolytic activities. For example, collagenases are known to be useful for isolating various cells from tissues. Deoxyribonucleases can digest single-stranded DNA and can minimize cell-clumping during isolation. Enzymes can be used alone or in combination. Serine protease are preferably used in a sequence following the use of other enzymes as they may degrade the other enzymes being used. The temperature and time of contact with serine proteases must be monitored. Serine proteases may be inhibited with alpha 2 microglobulin in serum and therefore the medium used for digestion is preferably serum-free. EDTA and DNase are commonly used and may improve yields or efficiencies. Preferred methods involve enzymatic treatment with for example collagenase and dispase, or collagenase, dispase, and hyaluronidase, and such methods are provided wherein in certain preferred embodiments, a mixture of collagenase and the neutral protease dispase are used in the dissociating step. More preferred are those methods which employ digestion in the presence of at least one collagenase from *Clostridium histolyticum*, and either of the protease activities, dispase and thermolysin. Still more preferred are methods employing digestion with both collagenase and dispase enzyme activities. Also preferred are methods which include digestion with a hyaluronidase activity in addition to collagenase and dispase activities. The skilled artisan will appreciate that many such enzyme treatments are known in the art for isolating cells from various tissue sources. For example, the LIB ERASE BLENDZYME (Roche) series of enzyme combinations of collagenase and neutral protease are very useful and may be used in the instant methods. Other sources of enzymes are known, and the skilled artisan may also obtain such enzymes directly from their natural sources. The skilled artisan is also well-equipped to assess new, or additional enzymes or enzyme combinations for their utility in isolating the cells of the invention. Preferred enzyme treatments are 0.5, 1, 1.5, or 2 hours long or longer. In other preferred embodiments, the tissue is incubated at 37.degree. C. during the enzyme treatment of the dissociation step. Diluting the digest may also improve yields of cells as cells may be trapped within a viscous digest.

While the use of enzyme activities is presently preferred, it is not required for isolation methods as provided herein. Methods based on mechanical separation alone may be successful in isolating the instant cells from the umbilicus as discussed above.

The cells can be resuspended after the tissue is dissociated into any culture medium as discussed herein above. Cells may be resuspended following a centrifugation step to separate out the cells from tissue or other debris. Resuspension may involve mechanical methods of resuspending, or simply the addition of culture medium to the cells.

Providing the growth conditions allows for a wide range of options as to culture medium, supplements, atmospheric conditions, and relative humidity for the cells. A preferred temperature is 37.degree. C., however the temperature may range from about 35.degree. C. to 39.degree. C. depending on the other culture conditions and desired use of the cells or culture.

Presently preferred are methods which provide cells which require no exogenous growth factors, except as are available in the supplemental serum provided with the Growth Medium. Also provided herein are methods of deriving umbilical cells capable of expansion in the absence of particular growth factors. The methods are similar to the method above, however they require that the particular growth factors (for which the cells have no requirement) be absent in the culture medium in which the cells are ultimately resuspended and grown in. In this sense, the method is selective for those cells capable of division in the absence of the particular growth factors. Preferred cells in some embodiments are capable of growth and expansion in chemically-defined growth media with no serum added. In such cases, the cells may require certain growth factors, which can be added to the medium to support and sustain the cells. Presently preferred factors to be added for growth on serum-free media include one or more of FGF, EGF, IGF, and PDGF. In more preferred embodiments, two, three or all four of the factors are add to serum free or chemically defined media. In other embodiments, LIF is added to serum-free medium to support or improve growth of the cells.

Also provided are methods wherein the cells can expand in the presence of from about 5% to about 20% oxygen in their atmosphere. Methods to obtain cells that require L-valine require that cells be cultured in the presence of L-valine. After a cell is obtained, its need for L-valine can be tested and confirmed by growing on D-valine containing medium that lacks the L-isomer.

Methods are provided wherein the cells can undergo at least 25, 30, 35, or 40 doublings prior to reaching a senescent state. Methods for deriving cells capable of doubling to reach $10^{14}$ cells or more are provided. Preferred are those methods which derive cells that can double sufficiently to produce at least about $10^{14}$, $10^{15}$, $10^{16}$, or $10^{17}$ or more cells when seeded at from about $10^{3}$ to about $10^{6}$ cells/cm·sup.2 in culture. Preferably these cell numbers are produced within 80, 70, or 60 days or less. In one embodiment, cord tissue mesenchymal stem cells are isolated and expanded, and possess one or more markers selected from a group comprising of CD10, CD13, CD44, CD73, CD90, CD141, PDGFr-alpha, or HLA-A,B,C. In addition, the cells do not produce one or more of CD31, CD34, CD45, CD117, CD141, or HLA-DR,DP, DQ.

In one embodiment, bone marrow MSC lots are generated, means of generating BM MSC are known in the literature and examples are incorporated by reference.

In one embodiment BM-MSC are generated as follows
1. 500 mL Isolation Buffer is prepared (PBS+2% FBS+2 mM EDTA) using sterile components or filtering Isolation Buffer through a 0.2 micron filter. Once made, the Isolation Buffer was stored at 2-8.degree. C.
2. The total number of nucleated cells in the BM sample is counted by taking 10 .mu·L BM and diluting it $\frac{1}{50}$-$\frac{1}{100}$ with 3% Acetic Acid with Methylene Blue (STEMCELL Catalog #07060). Cells are counted using a hemacytometer.
3. 50 mL Isolation Buffer is warmed to room temperature for 20 minutes prior to use and bone marrow was diluted $\frac{5}{14}$ final dilution with room temperature Isolation Buffer (e.g. 25 mL BM was diluted with 45 mL Isolation Buffer for a total volume of 70 mL).
4. In three 50 mL conical tubes (BD Catalog #352070), 17 mL Ficoll-Paque.™. PLUS (Catalog #07907/07957) is pipetted into each tube. About 23 mL of the diluted BM from step 3 was carefully layered on top of the Ficoll-Paque.™. PLUS in each tube.
5. The tubes are centrifuged at room temperature (15-25.degree. C.) for 30 minutes at 300.times·g in a bench top centrifuge with the brake off.
6. The upper plasma layer is removed and discarded without disturbing the plasma:Ficoll-Paque.™. PLUS interface. The mononuclear cells located at the interface layer are carefully removed and placed in a new 50 mL conical tube. Mononuclear cells are resuspended with 40 mL cold (2-8.degree. C.) Isolation Buffer and mixed gently by pipetting.
7. Cells were centrifuged at 300.times·g for 10 minutes at room temperature in a bench top centrifuge with the brake on. The supernatant is removed and the cell pellet resuspended in 1-2 mL cold Isolation Buffer.
8. Cells were diluted 1/50 in 3% Acetic Acid with Methylene Blue and the total number of nucleated cells counted using a hemacytometer.
9. Cells are diluted in Complete Human MesenCult®-Proliferation medium (STEMCELL catalog #05411) at a final concentration of $1.\times 10.^{6}$ cells/mL.
10. BM-derived cells were ready for expansion and CFU-F assays in the presence of GW2580, which can then be used for specific applications.

In one embodiment, MSC are generated according to protocols previously utilized for treatment of patients utilizing bone marrow derived MSC. Specifically, bone marrow is aspirated (10-30 ml) under local anesthesia (with or without sedation) from the posterior iliac crest, collected into sodium heparin containing tubes and transferred to a Good Manufacturing Practices (GMP) clean room. Bone marrow cells are washed with a washing solution such as Dulbecco's phosphate-buffered saline (DPBS), RPMI, or PBS supplemented with autologous patient plasma and layered on to 25 ml of Percoll (1.073 g/ml) at a concentration of approximately 1-2 ' 107 cells/ml. Subsequently the cells are centrifuged at 900 g for approximately 30 min or a time period sufficient to achieve separation of mononuclear cells from debris and erythrocytes. Said cells are then washed with PBS and plated at a density of approximately 1' 106 cells per ml in 175 cm2 tissue culture flasks in DMEM with 10% FCS with flasks subsequently being loaded with a minimum of 30 million bone marrow mononuclear cells. The MSCs are allowed to adhere for 72 h followed by media changes every 3-4 days. Adherent cells are removed with 0.05% trypsin-EDTA and replated at a density of 1' 106 per 175 cm2. Said bone marrow MSC may be administered intravenously, or in a preferred embodiment, intrathecally in a patient suffering radiation associated neurodegenerative manifestations. Although doses may be determined by one of skill in the art, and are dependent on various patient characteristics, intravenous administration may be performed at concentrations ranging from 1-10 million MSC per kilogram, with a preferred dose of approximately 2-5 million cells per kilogram.

In order to determine the quality of MSC cultures, flow cytometry is performed on all cultures for surface expression of SH-2, SH-3, SH-4 MSC markers and lack of contaminating CD14- and CD-45 positive cells. Cells were detached with 0.05% trypsin-EDTA, washed with DPBS+2% bovine albumin, fixed in 1% paraformaldehyde, blocked in 10% serum, incubated separately with primary SH-2, SH-3 and SH-4 antibodies followed by PE-conjugated anti-mouse IgG(H+L) antibody. Confluent MSC in 175 cm2 flasks are washed with Tyrode's salt solution, incubated with medium 199 (M199) for 60 min, and detached with 0.05% trypsin-EDTA (Gibco). Cells from 10 flasks were detached at a time and MSCs were resuspended in 40 ml of M199+1% human serum albumin (HSA; American Red Cross, Washington DC, USA). MSCs harvested from each 10-flask set were stored for up to 4 h at 4° C. and combined at the end of the harvest. A total of 2-10' 106 MSC/kg were resuspended in M199+1% HSA and centrifuged at 460 g for 10 min at 20° C. Cell pellets were resuspended in fresh M199+1% HSA media and centrifuged at 460 g for 10 min at 20° C. for three additional times. Total harvest time was 2-4 h based on MSC yield per flask and the target dose. Harvested MSC were cryopreserved in Cryocyte (Baxter, Deerfield, IL, USA) freezing bags using a rate controlled freezer at a final concentration of 10% DMSO (Research Industries, Salt Lake City, UT, USA) and 5% HSA. On the day of infusion cryopreserved units were thawed at the bedside in a 37° C. water bath and transferred into 60 ml syringes within 5 min and infused intravenously into patients over 10-15 min. Patients are premedicated with 325-650 mg acetaminophen and 12.5-25 mg of diphenhydramine orally. Blood pressure, pulse, respiratory rate, temperature and oxygen saturation are monitored at the time of infusion and every 15 min thereafter for 3 h followed by every 2 h for 6 h.

Within the context of the invention, exosomes and microparticles may be used interchangeably. Exosomes from MSC may be generated from a mesenchymal stem cell conditioned medium (MSC-CM). Said exosomes are used in the context of the invention to reprogram immunocytes ex vivo or in vivo. Said particle may be isolated for example by being separated from non-associated components based on any property of the particle. For example, the particle may be isolated based on molecular weight, size, shape, composition or biological activity. The conditioned medium may be filtered or concentrated or both during, prior to or subsequent to separation. For example, it may be filtered through a membrane, for example one with a size or molecular weight cut-off. It may be subject to tangential force filtration or ultrafiltration. Filtration of conditioned media is described in the following and incorporated by reference [180]. For example, filtration with a membrane of a suitable molecular weight or size cutoff. The conditioned medium, optionally filtered or concentrated or both, may be subject to further separation means, such as column chromatography. For example, high performance liquid chromatography (HPLC) with various columns may be used. The columns may be size exclusion columns or binding columns. One or more properties or biological activities of the particle may be used to track its activity during fractionation of the mesenchymal stem cell conditioned medium (MSC-CM). As an example, light scattering, refractive index, dynamic light scattering or UV-visible detectors may be used to follow the particles. For example, a therapeutic activity such as anti-rheumatic activity may be used to track the activity during fractionation. In one embodiment antirheumatic activity is assessed by ability to inhibit TNF-alpha production from stimulated monocytes or monocytic lineage cell such as macrophages or dendritic cells.

In one aspect of the invention MSC are cultured for about 1, 2, 3, 4, 5, 6, 7, 8, 9, 10 days or more, for example 3 days. The conditioned medium may be obtained by separating the cells from the medium. The conditioned medium may be centrifuged, for example at 500 g. it may be concentrated by filtration through a membrane. The membrane may comprise a >1000 kDa membrane. The conditioned medium may be concentrated about 50 times or more. The conditioned medium may be subject to liquid chromatography such as HPLC. The conditioned medium may be separated by size exclusion. Any size exclusion matrix such as Sepharose may be used. As an example, a TSK Guard column SWXL, $6.\times 40$ mm or a TSK gel G4000 SWXL, $7.8.\times 300$ mm may be employed. The eluent buffer may comprise any physiological medium such as saline. It may comprise 20 mM phosphate buffer with 150 mM of NaCl at pH 7.2. The chromatography system may be equilibrated at a flow rate of 0.5 ml/min. The elution mode may be isocratic. UV absorbance at 220 nm may be used to track the progress of elution. Fractions may be examined for dynamic light scattering (DLS) using a quasi-elastic light scattering (QELS) detector. Fractions which are found to exhibit dynamic light scattering may be retained. For example, a fraction which is produced by the general method as described above, and which elutes with a retention time of 11-13 minutes, such as 12 minutes, is found to exhibit dynamic light scattering. The r.sub.h of particles in this peak is about 45-55 nm. Such fractions comprise mesenchymal stem cell particles such as exosomes.

MSC can be prepared from a variety of tissues, such as bone marrow cells [181-187], umbilical cord tissue [188-190], peripheral blood [191-193], amniotic membrane [194], amniotic fluid, mobilized peripheral blood [195], adipose tissue [196, 197], endometrium and other tissues. When tissue sources of MSC are used said tissue isolates from which the Reprogrammed immune cells are isolated comprise a mixed populations of cells. Reprogrammed immune cells constitute a very small percentage in these initial populations. They must be purified away from the other cells before they can be expanded in culture sufficiently to obtain enough cells for therapeutic applications.

The choice of formulation for administering reprogrammed immune cells for a given application will depend on a variety of factors. Prominent among these will be the species of subject, the nature of the disorder, dysfunction, or disease being treated and its state and distribution in the subject, the nature of other therapies and agents that are being administered, the optimum route for administration of the reprogrammed immune cells, survivability of reprogrammed immune cells via the route, the dosing regimen, and other factors that will be apparent to those skilled in the art. In particular, for instance, the choice of suitable carriers and other additives will depend on the exact route of administration and the nature of the particular dosage form, for example, liquid dosage form (e.g., whether the composition is to be formulated into a solution, a suspension, gel or another liquid form, such as a time release form or liquid-filled form).

For example, cell survival can be an important determinant of the efficacy of cell-based therapies. This is true for both primary and adjunctive therapies. Another concern arises when target sites are inhospitable to cell seeding and cell growth. This may impede access to the site and/or engraftment there of therapeutic Reprogrammed immune cells. Various embodiments of the invention comprise measures to increase cell survival and/or to overcome problems posed by barriers to seeding and/or growth.

Examples of compositions comprising reprogrammed immune cells include liquid preparations, including suspensions and preparations for intramuscular or intravenous administration (e.g., injectable administration), such as sterile suspensions or emulsions. Such compositions may comprise an admixture of Reprogrammed immune cells with a suitable carrier, diluent, or excipient such as sterile water, physiological saline, glucose, dextrose, or the like. The compositions can also be lyophilized. The compositions can contain auxiliary substances such as wetting or emulsifying agents, pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE," 17th edition, 1985, incorporated herein by reference, may be consulted to prepare suitable preparations, without undue experimentation.

Compositions of the invention often are conveniently provided as liquid preparations, e.g., isotonic aqueous solutions, suspensions, emulsions, or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues.

Various additives often will be included to enhance the stability, sterility, and isotonicity of the compositions, such as antimicrobial preservatives, antioxidants, chelating agents, and buffers, among others. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents that delay absorption, for example, aluminum monostearate, and gelatin. According to the present invention, however, any vehicle, diluent, or additive used would have to be compatible with the cells.

Reprogrammed immune cells solutions, suspensions, and gels normally contain a major amount of water (preferably purified, sterilized water) in addition to the cells. Minor amounts of other ingredients such as pH adjusters (e.g., a base such as NaOH), emulsifiers or dispersing agents, buffering agents, preservatives, wetting agents and jelling agents (e.g., methylcellulose) may also be present. In some embodiments of the invention, treatment of viral associated cardiac damage is disclosed using immune cells that have been reprogrammed with regenerative cells. Some patients hospitalized for COVID-19 have had increased levels of cardiac enzyme or markers that indicate their hearts are at least temporarily damaged. Also, cardiac damage is more common in patients who have severe COVID-19 disease.

Typically, the compositions will be isotonic, i.e., they will have the same osmotic pressure as blood and lacrimal fluid when properly prepared for administration.

The desired isotonicity of the compositions of this invention may be accomplished using sodium chloride, or other pharmaceutically acceptable agents such as dextrose, boric acid, sodium tartrate, propylene glycol, or other inorganic or organic solutes. Sodium chloride is preferred particularly for buffers containing sodium ions.

Viscosity of the compositions, if desired, can be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount, which will achieve the selected viscosity. Viscous compositions are normally prepared from solutions by the addition of such thickening agents.

A pharmaceutically acceptable preservative or cell stabilizer can be employed to increase the life of reprogrammed immune cells compositions. If such preservatives are included, it is well within the purview of the skilled artisan to select compositions that will not affect the viability or efficacy of the reprogrammed immune cells.

Those skilled in the art will recognize that the components of the compositions should be chemically inert. This will present no problem to those skilled in chemical and pharmaceutical principles. Problems can be readily avoided by reference to standard texts or by simple experiments (not involving undue experimentation) using information provided by the disclosure, the documents cited herein, and generally available in the art.

Sterile injectable solutions can be prepared by incorporating the cells utilized in practicing the present invention in the required amount of the appropriate solvent with various amounts of the other ingredients, as desired.

In some embodiments, reprogrammed immune cells are formulated in a unit dosage injectable form, such as a solution, suspension, or emulsion. Pharmaceutical formulations suitable for injection of Reprogrammed immune cells typically are sterile aqueous solutions and dispersions. Carriers for injectable formulations can be a solvent or dispersing medium containing, for example, water, saline, phosphate buffered saline, polyol (for example, glycerol, propylene glycol, liquid polyethylene glycol, and the like), and suitable mixtures thereof.

The skilled artisan can readily determine the amount of cells and optional additives, vehicles, and/or carrier in compositions to be administered in methods of the invention. Typically, any additives (in addition to the cells) are present in an amount of 0.001 to 50 wt % in solution, such as in phosphate buffered saline. The active ingredient is present in the order of micrograms to milligrams, such as about 0.0001 to about 5 wt %, preferably about 0.0001 to about 1 wt %, most preferably about 0.0001 to about 0.05 wt % or about 0.001 to about 20 wt %, preferably about 0.01 to about 10 wt %, and most preferably about 0.05 to about 5 wt %.

For any composition to be administered to an animal or human, and for any particular method of administration, it is preferred to determine therefore: toxicity, such as by determining the lethal dose (LD) and LD50 in a suitable animal model, e.g., rodent such as mouse or rat; and, the dosage of the composition(s), concentration of components therein, and timing of administering the composition(s), which elicit a suitable response. Such determinations do not require undue experimentation from the knowledge of the skilled artisan, this disclosure, and the documents cited herein. And, the time for sequential administrations can be ascertained without undue experimentation.

In some embodiments Reprogrammed immune cells are encapsulated for administration, particularly where encapsulation enhances the effectiveness of the therapy, or provides advantages in handling and/or shelf life. Encapsulation in some embodiments where it increases the efficacy of the cell mediated immunosuppression may, as a result, also reduce the need for immunosuppressive drug therapy.

Also, encapsulation in some embodiments provides a barrier to a subject's immune system that may further reduce a subject's immune response to the Reprogrammed immune cells (which generally are not immunogenic or are only weakly immunogenic in allogeneic transplants), thereby reducing any graft rejection or inflammation that might occur upon administration of the cells.

In a variety of embodiments where reprogrammed immune cells are administered in admixture with cells of another type, which are more typically immunogenic in an allogeneic or xenogeneic setting, encapsulation may reduce or eliminate adverse host immune responses to the non-reprogrammed immune cells cells and/or GVHD that might occur in an immunocompromised host if the admixed cells are immunocompetent and recognize the host as non-self.

Reprogrammed immune cells may be encapsulated by membranes, as well as capsules, prior to implantation. It is contemplated that any of the many methods of cell encapsulation available may be employed. In some embodiments, cells are individually encapsulated. In some embodiments, many cells are encapsulated within the same membrane. In embodiments in which the cells are to be removed following implantation, a relatively large size structure encapsulating many cells, such as within a single membrane, may provide a convenient means for retrieval.

A wide variety of materials may be used in various embodiments for microencapsulation of Reprogrammed immune cells. Such materials include, for example, polymer capsules, alginate-poly-L-lysine-alginate microcapsules, barium poly-L-lysine alginate capsules, barium alginate capsules, polyacrylonitrile/polyvinylchloride (PAN/PVC) hollow fibers, and polyethersulfone (PES) hollow fibers.

Techniques for microencapsulation of cells that may be used for administration of Reprogrammed immune cells are known to those of skill in the art and are described, for example, in Chang, P., et al., 1999; Matthew, H. W., et al., 1991; Yanagi, K., et al., 1989; Cal Z. H., et al., 1988; Chang, T. M., 1992 and in U.S. Pat. No. 5,639,275 (which, for example, describes a biocompatible capsule for long-term maintenance of cells that stably express biologically active molecules. Additional methods of encapsulation are in European Patent Publication No. 301,777 and U.S. Pat. Nos. 4,353,888; 4,744,933; 4,749,620; 4,814,274; 5,084,350; 5,089,272; 5,578,442; 5,639,275; and 5,676,943. All of the foregoing are incorporated herein by reference in parts pertinent to encapsulation of Reprogrammed immune cells.

Certain embodiments incorporate Reprogrammed immune cells into a polymer, such as a biopolymer or synthetic polymer. Examples of biopolymers include, but are not limited to, fibronectin, fibin, fibrinogen, thrombin, collagen, and proteoglycans. Other factors, such as the cytokines discussed above, can also be incorporated into the polymer. In other embodiments of the invention, Reprogrammed immune cells may be incorporated in the interstices of a three-dimensional gel. A large polymer or gel, typically, will be surgically implanted. A polymer or gel that can be formulated in small enough particles or fibers can be administered by other common, more convenient, non-surgical routes.

Pharmaceutical compositions of the invention may be prepared in many forms that include tablets, hard or soft gelatin capsules, aqueous solutions, suspensions, and liposomes and other slow-release formulations, such as shaped polymeric gels. Oral liquid pharmaceutical compositions may be in the form of, for example, aqueous or oily suspensions, solutions, emulsions, syrups, or elixirs, or may be presented as a dry product for constitution with water or other suitable vehicle before use. Such liquid pharmaceutical compositions may contain conventional additives such as suspending agents, emulsifying agents, non-aqueous vehicles (which may include edible oils), or preservatives. An oral dosage form may be formulated such that cells are released into the intestine after passing through the stomach. Such formulations are described in U.S. Pat. No. 6,306,434 and in the references contained therein.

Pharmaceutical compositions suitable for rectal administration can be prepared as unit dose suppositories. Suitable carriers include saline solution and other materials commonly used in the art.

For administration by inhalation, cells can be conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide, or other suitable gas. In the case of a pressurized aerosol, the dosage unit may be determined by providing a valve to deliver a metered amount.

Alternatively, for administration by inhalation or insufflation, a means may take the form of a dry powder composition, for example, a powder mix of a modulator and a suitable powder base such as lactose or starch. The powder composition may be presented in unit dosage form in, for example, capsules or cartridges or, e.g., gelatin or blister packs from which the powder may be administered with the aid of an inhalator or insufflator. For intra-nasal administration, cells may be administered via a liquid spray, such as via a plastic bottle atomizer.

Reprogrammed immune cells may be administered with other pharmaceutically active agents. In some embodiments one or more of such agents are formulated together with Reprogrammed immune cells for administration. In some embodiments the Reprogrammed immune cells and the one or more agents are in separate formulations. In some embodiments the compositions comprising the Reprogrammed immune cells and/or the one or more agents are formulated with regard to adjunctive use with one another.

Reprogrammed immune cells may be administered in a formulation comprising a immunosuppressive agents, such as any combination of any number of a corticosteroid, cyclosporin A, a cyclosporin-like immunosuppressive agent, cyclophosphamide, antithymocyte globulin, azathioprine, rapamycin, FK-506, and a macrolide-like immunosuppressive agent other than FK-506 and rapamycin. In certain embodiments, such agents include a corticosteroid, cyclosporin A, azathioprine, cyclophosphamide, rapamycin, and/or FK-506. Immunosuppressive agents in accordance with the foregoing may be the only such additional agents or may be combined with other agents, such as other agents noted herein. Other immunosuppressive agents include Tacrolimus, Mycophenolate mofetil, and Sirolimus.

Such agents also include antibiotic agents, antifungal agents, and antiviral agents, to name just a few other pharmacologically active substances and compositions that may be used in accordance with embodiments of the invention.

Typical antibiotics or anti-mycotic compounds include, but are not limited to, penicillin, streptomycin, amphotericin, ampicillin, gentamicin, kanamycin, mycophenolic acid, nalidixic acid, neomycin, nystatin, paromomycin, polymyxin, puromycin, rifampicin, spectinomycin, tetracycline, tylosin, zeocin, and cephalosporins, aminoglycosides, and echinocandins.

Further additives of this type relate to the fact that Reprogrammed immune cells, like other stems cells, following administration to a subject may "home" to an environment favorable to their growth and function. Such "homing" often concentrates the cells at sites where they are needed, such as sites of immune disorder, dysfunction, or disease. A number of substances are known to stimulate homing. They include growth factors and trophic signaling agents, such as cytokines. They may be used to promote homing of Reprogrammed immune cells to therapeutically targeted sites. They may be administered to a subject prior to treatment with Reprogrammed immune cells, together with reprogrammed immune cells, or after reprogrammed immune cells are administered.

Certain cytokines, for instance, alter or affect the migration of reprogrammed immune cells or their differentiated counterparts to sites in need of therapy, such as immunocompromised sites. Cytokines that may be used in this regard include, but are not limited to, stromal cell derived factor-1 (SDF-1), stem cell factor (SCF), angiopoietin-1, placenta-derived growth factor (PIGF), granulocyte-colony stimulating factor (G-CSF), cytokines that stimulate expression of endothelial adhesion molecules such as ICAMs and VCAMs, and cytokines that engender or facilitate homing.

They may be administered to a subject as a pre-treatment, along with Reprogrammed immune cells, or after reprogrammed immune cells have been administered, to promote homing to desired sites and to achieve improved therapeutic effect, either by improved homing or by other mechanisms. Such factors may be combined with Reprogrammed immune cells in a formulation suitable for them to be administered together. Alternatively, such factors may be formulated and administered separately.

Order of administration, formulations, doses, frequency of dosing, and routes of administration of factors (such as the cytokines discussed above) and Reprogrammed immune cells generally will vary with the disorder or disease being treated, its severity, the subject, other therapies that are being administered, the stage of the disorder or disease, and prognostic factors, among others. General regimens that have been established for other treatments provide a framework for determining appropriate dosing in reprogrammed immune cells-mediated direct or adjunctive therapy. These, together with the additional information provided herein, will enable the skilled artisan to determine appropriate administration procedures in accordance with embodiments of the invention, without undue experimentation.

Reprogrammed immune cells can be administered to a subject by any of a variety of routes known to those skilled in the art that may be used to administer cells to a subject.

Among methods that may be used in this regard in embodiments of the invention are methods for administering reprogrammed immune cells by a parenteral route. Parenteral routes of administration useful in various embodiments of the invention include, among others, administration by intravenous, intraarterial, intracardiac, intraspinal, intrathecal, intraosseous, intraarticular, intrasynovial, intracutaneous, intradermal, subcutaneous, and/or intramuscular injection. In some embodiments intravenous, intraarterial, intracutaneous, intradermal, subcutaneous and/or intramuscular injection are used. In some embodiments intravenous, intraarterial, intracutaneous, subcutaneous, and/or intramuscular injection are used.

In various embodiments of the invention reprogrammed immune cells are administered by systemic injection. Systemic injection, such as intravenous injection, offers one of the simplest and least invasive routes for administering reprogrammed immune cells. In some cases, these routes may require high reprogrammed immune cells doses for optimal effectiveness and/or homing by the reprogrammed immune cells to the target sites. In a variety of embodiments reprogrammed immune cells may be administered by targeted and/or localized injections to ensure optimum effect at the target sites.

Reprogrammed immune cells may be administered to the subject through a hypodermic needle by a syringe in some embodiments of the invention. In various embodiments, reprogrammed immune cells are administered to the subject through a catheter. In a variety of embodiments, reprogrammed immune cells are administered by surgical implantation. Further in this regard, in various embodiments of the invention, Reprogrammed immune cells are administered to the subject by implantation using an arthroscopic procedure. In some embodiments Reprogrammed immune cells are administered to the subject in or on a solid support, such as a polymer or gel. In various embodiments, Reprogrammed immune cells are administered to the subject in an encapsulated form.

In additional embodiments of the invention, Reprogrammed immune cells are suitably formulated for oral, rectal, epicutaneous, ocular, nasal, and/or pulmonary delivery and are administered accordingly.

Compositions can be administered in dosages and by techniques well known to those skilled in the medical and veterinary arts taking into consideration such factors as the age, sex, weight, and condition of the particular patient, and the formulation that will be administered (e.g., solid vs. liquid). Doses for humans or other mammals can be determined without undue experimentation by the skilled artisan, from this disclosure, the documents cited herein, and the knowledge in the art.

The dose of reprogrammed immune cells appropriate to be used in accordance with various embodiments of the invention will depend on numerous factors. It may vary considerably for different circumstances. The parameters that will determine optimal doses of reprogrammed immune cells to be administered for primary and adjunctive therapy generally will include some or all of the following: the disease being treated and its stage; the species of the subject, their health, gender, age, weight, and metabolic rate; the subject's immunocompetence; other therapies being administered; and expected potential complications from the subject's history or genotype. The parameters may also include: whether the Reprogrammed immune cells are syngeneic, autologous, allogeneic, or xenogeneic; their potency (specific activity); the site and/or distribution that must be targeted for the Reprogrammed immune cells to be effective; and such characteristics of the site such as accessibility to Reprogrammed immune cells and/or engraftment of Reprogrammed immune cells. Additional parameters include co-administration with Reprogrammed immune cells of other factors (such as growth factors and cytokines). The optimal dose in a given situation also will take into consideration the way in which the cells are formulated, the way they are administered, and the degree to which the cells will be localized at the target sites following administration. Finally, the determination of optimal dosing necessarily will provide an effective dose that is neither below the threshold of maximal beneficial effect nor above the threshold where the deleterious effects associated with the dose of Reprogrammed immune cells outweighs the advantages of the increased dose.

The optimal dose of reprogrammed immune cells for some embodiments will be in the range of doses used for autologous, mononuclear bone marrow transplantation. For fairly pure preparations of reprogrammed immune cells, optimal doses in various embodiments will range from $10^4$ to $10^8$ reprogrammed immune cells cells/kg of recipient mass per administration. In some embodiments the optimal dose per administration will be between $10^5$ to $10^7$ reprogrammed immune cells cells/kg. In many embodiments the optimal dose per administration will be $5 \times 10^5$ to $5 \times 10^6$ reprogrammed immune cells cells/kg. By way of reference, higher doses in the foregoing are analogous to the doses of nucleated cells used in autologous mononuclear bone marrow transplantation. Some of the lower doses are analogous to the number of $CD34^+$ cells/kg used in autologous mononuclear bone marrow transplantation.

It is to be appreciated that a single dose may be delivered all at once, fractionally, or continuously over a period of time. The entire dose also may be delivered to a single location or spread fractionally over several locations.

In various embodiments, Reprogrammed immune cells may be administered in an initial dose, and thereafter maintained by further administration of Reprogrammed immune cells. Reprogrammed immune cells may be administered by one method initially, and thereafter administered by the same method or one or more different methods. The subject's MSC levels can be maintained by the ongoing administration of the cells. Various embodiments administer the Reprogrammed immune cells either initially or to maintain their level in the subject or both by intravenous injection. In a variety of embodiments, other forms of administration, are used, dependent upon the patient's condition and other factors, discussed elsewhere herein.

It is noted that human subjects are treated generally longer than experimental animals; but, treatment generally has a length proportional to the length of the disease process and the effectiveness of the treatment. Those skilled in the art will take this into account in using the results of other procedures carried out in humans and/or in animals, such as rats, mice, non-human primates, and the like, to determine appropriate doses for humans. Such determinations, based on these considerations and taking into account guidance provided by the present disclosure and the prior art will enable the skilled artisan to do so without undue experimentation.

Suitable regimens for initial administration and further doses or for sequential administrations may all be the same or may be variable. Appropriate regiments can be ascertained by the skilled artisan, from this disclosure, the documents cited herein, and the knowledge in the art.

The dose, frequency, and duration of treatment will depend on many factors, including the nature of the disease, the subject, and other therapies that may be administered. Accordingly, a wide variety of regimens may be used to administer Reprogrammed immune cells.

In some embodiments Reprogrammed immune cells are administered to a subject in one dose. In others Reprogrammed immune cells are administered to a subject in a series of two or more doses in succession. In some other embodiments wherein Reprogrammed immune cells are administered in a single dose, in two doses, and/or more than two doses, the doses may be the same or different, and they are administered with equal or with unequal intervals between them.

Reprogrammed immune cells may be administered in many frequencies over a wide range of times. In some embodiments, reprogrammed immune cells are administered over a period of less than one day. In other embodiment they are administered over two, three, four, five, or six days. In some embodiments Reprogrammed immune cells are administered one or more times per week, over a period of weeks. In other embodiments they are administered over a period of weeks for one to several months. In various embodiments they may be administered over a period of months. In others they may be administered over a period of one or more years. Generally lengths of treatment will be proportional to the length of the disease process, the effectiveness of the therapies being applied, and the condition and response of the subject being treated.

The immunomodulatory properties of reprogrammed immune cells may be used in treating a wide variety of disorders, dysfunctions and diseases, such as those that, intrinsically, as a secondary effect or as a side effect of treatment, present with deleterious immune system processes and effects. Several illustrations are discussed below.

In a variety of embodiments involving transplant therapies, reprogrammed immune cells can be used alone for an immunosuppressive purpose, or together with other agents. Reprogrammed immune cells can be administered before, during, or after one or more transplants. If administered during transplant, reprogrammed immune cells can be administered separately or together with transplant material. If separately administered, the Reprogrammed immune cells can be administered sequentially or simultaneously with the other transplant materials. Furthermore, Reprogrammed immune cells may be administered well in advance of the transplant and/or well after, alternatively to or in addition to administration at or about the same time as administration of the transplant.

Other agents that can be used in conjunction with reprogrammed immune cells, in transplantation therapies in particular, include immunomodulatory agents, such as those described elsewhere herein, particularly immunosuppressive agents, more particularly those described elsewhere herein, especially in this regard, one or more of a corticosteroid, cyclosporin A, a cyclosporin-like immunosuppressive compound, azathioprine, cyclophosphamide, methotrexate, and an immunosuppressive monoclonal antibody agent.

Reprogrammed immune cells can modulate immune responses. In particular in this regard, it has been found that Reprogrammed immune cells can suppress immune responses, including but not limited to immune responses involved in, for example, HVG response and GVHD, to name just two. In an even more detailed particular in this regard, it has been found that Reprogrammed immune cells can suppress proliferation of T-cells, even in the presence of potent T-cell stimulators, such as Concanavalin A and allogeneic or xenogeneic stimulator cells.

Moreover, it has been found that even relatively small amounts of reprogrammed immune cells can suppress these responses. Indeed, only 3% Reprogrammed immune cells in mixed lymphocyte reactions is sufficient to reduce T-cell response by 50% in vitro. Embodiments of the invention relate to using reprogrammed immune cells immunomodulation to treat an immune dysfunction, disorder, or disease, either solely, or as an adjunctive therapy. Embodiments in this regard relate to congenital immune deficiencies and autoimmune dysfunctions, disorders, and diseases. Various embodiments relate, in this regard, to using Reprogrammed immune cells to treat, solely or adjunctively, Crohn's disease, Guillain-Barre syndrome, lupus erythematosus (also called "SLE" and systemic lupus erythematosus), multiple sclerosis, myasthenia gravis, optic neuritis, psoriasis, rheumatoid arthritis, Graves' disease, Hashimoto's disease, Ord's thyroiditis, diabetes mellitus (type 1), Reiter's syndrome, autoimmune hepatitis, primary biliary cirrhosis, antiphospholipid antibody syndrome ("APS"), opsoclonus-myoclonus syndrome ("OMS"), temporal arteritis, acute disseminated encephalomyelitis ("ADEM" and "ADE"), Goodpasture's, syndrome, Wegener's granulomatosis, celiac disease, pemphigus, polyarthritis, autism, autism spectrum disorder, post traumatic stress disorder, and warm autoimmune hemolytic anemia.

Particular embodiments among these relate to Crohn's disease, lupus erythematosus (also called "SLE" and systemic lupus erythematosus), multiple sclerosis, myasthenia gravis, psoriasis, rheumatoid arthritis, Graves' disease, Hashimoto's disease, diabetes mellitus (type 1), Reiter's syndrome, primary biliary cirrhosis, celiac disease, polyarhritis, and warm autoimmune hemolytic anemia.

In addition, reprogrammed immune cells are used in a variety of embodiments in this regard, solely and, typically, adjunctively, to treat a variety of diseases thought to have an autoimmune component, including but not limited to embodiments that may be used to treat endometriosis, interstitial cystitis, neuromyotonia, scleroderma, progressive systemic scleroderma, vitiligo, vulvodynia, Chagas' disease, sarcoidosis, chronic fatigue syndrome, and dysautonomia.

Inherited immune system disorders include Severe Combined Immunodeficiency (SCID) including but not limited to SCID with Adenosine Deaminase Deficiency (ADA-SCID), SCID which is X-linked, SCID with absence of T & B Cells, SCID with absence of T Cells, Normal B Cells, Omenn Syndrome, Neutropenias including but not limited to Kostmann Syndrome, Myelokathexis; Ataxia-Telangiectasia, Bare Lymphocyte Syndrome, Common Variable Immunodeficiency, DiGeorge Syndrome, Leukocyte Adhesion Deficiency; and phagocyte Disorders (phagocytes are immune system cells that can engulf and kill foreign organisms) including but not limited to Chediak-Higashi Syndrome, Chronic Granulomatous Disease, Neutrophil Actin Deficiency, Reticular Dysgenesis. Reprogrammed immune cells may be administered adjunctively to a treatment for any of the foregoing diseases.

In one embodiment tissue culture supernatant is derived from cultures of reprogrammed immune cells and utilized for therapeutic applications. Use of tissue culture supernatant is described in the following patents and incorporated by U.S. Pat. Nos. 8,703,710; 9,192,632; 6,642,048; 7,790,455; 9,192,632; and the following patent applications; 20160022738; 20160000699; 20150024483; 20130251670; 20120294949; 20120276215; 20120195969; 20110293583; 20110171182; 20110129447; 20100159588; 20080241112.

In some embodiments, the invention teaches the extraction of peripheral blood mononuclear cells from a patient with an infarct, culturing of said cells with allogeneic mesenchymal stem cells, and readminstration of the extracted recipient mononuclear cells. In some embodiments said mononuclear cells from said patient are first purified to obtain a population of T cells and said T cells are then re-infused into the patient after culture with said mesenchymal stem cells. In some embodiments a mitogen for T cells is added, wherein said mitogen allows for said T cells to possess cardioregenerative activity. In some embodiments said mitogen is interleukin-2. It should be noted that the ex vivo use of interleukin-2 should be guided on ability to induce expansion of T regulatory cells ex vivo.

In some embodiments the invention teaches administration of reprogrammed immune cells together with MSC. We provide some examples of the use of MSC for treatment of heart conditions, as well as the use of bone marrow stem cells.

One of the original descriptions of clinical stem cell use in the cardiac space was Strauer et al. who reported a case in which a 46-year-old patient received autologous bone marrow mononuclear cells by a percutaneous transluminal catheter placed in the infarct-related artery. Ten weeks after administration the transmural infarct area had been reduced from 24.6% to 15.7% of left ventricular circumference, while ejection fraction, cardiac index, and stroke volume had increased by 20-30% [198]. A subsequent paper in the same year reported administration of similar cells in 5 patients with advanced ischemia undergoing coronary artery bypass grafting. Cells were administered intramuscularly into areas deemed ungraftable and perfusion was assessed by imaging. Specific improvement in areas injected was documented in 3 of the 5 patients. Perhaps more importantly, no ectopic growths or adverse effects were reported at 1 year follow-up [199]. Since these pioneering studies, cardiac stem cell therapy has been used by numerous groups for numerous conditions causing heart failure. These can be broken down into: a) inhibiting post-acute myocardial infarction remodeling; b) stimulation of regeneration in chronically injured hearts; and c) induction of angiogenesis in coronary artery disease. The methods of administering stem cells have included the intracoronary, epicardial, and intravenous routes. Stem cells used to date are bone marrow mononuclear cells, mobilized peripheral blood stem cells, purified CD34 or CD133 cells, autologous mesenchymal stem cells, and allogeneic bone marrow and placental mesenchymal stem cells.

Several meta-analyses of ongoing clinical trials performed indicated that both hematopoietic and mesenchymal cells have promising clinical effects in various types of heart failure. Briefly, Abdel-Latif et al. described 999 patients enrolled in 18 independent controlled cardiac trials in which patients were treated with either unfractionated bone marrow cells, bone marrow mesenchymal, or mobilized peripheral blood [200]. They found that in comparison to controls, there was a statistically significant improvement in ejection fraction, reduction in infarct size, and left ventricular end-systolic volume. Importantly, no safety issues or serious treatment-associated adverse events were noted. In another such comprehensive review, Martin-Rendon et al. focused on bone marrow therapy for post-acute infarction trials. Of 13 randomized studies conducted, encompassing 811 participants, the authors of the review stated that more trials are needed to establish efficacy in terms of clinical endpoints such as death. However, the authors of the review did observe a consistent improvement in LVEF, as well as trends for decrease in left ventricular end-systolic and end-diastolic volumes and infarct size [201]. Three other meta-analyses of randomized trials in the area of bone marrow stem cell infusions also supported the conclusion of safety and mild but statistically significant improvement in LVEF [202-204]. These data suggest that stem cell therapy, both hematopoietic and mesenchymal, has clinical effects in various types of heart failure. Theoretically, the leap between these clinical trials and widespread implementation is more of a business question than a medical question. In order to postulate on the future of cardiac stem cell therapy, we will discuss several possible means of optimizing existing work.

However, the lack of concordance between emerging animal data showing low or undetectable contributions of BM cells to new cardiomyocyte formation [205, 206] and the contrasting clinical benefits derived in early uncontrolled trials [207-209] raises the question of what mechanism underlies contractile function improvement following human BM cell therapy. Mechanisms of cell benefit in addition to myogenesis might involve intrinsic remodeling of the ventricle in the absence of a direct cellular effect, improvement in contractile function and myocardial perfusion secondary to the primary revascularization procedure (in the case of stent placement or coronary bypass surgery), or impairment of myocyte death. Additional nonmyogenic contributions to BM cell improvements in cardiac function might include vasculogenic effects of angioblastic, myeloid, mesenchymal, or other stem cells resident in the marrow and heart, or paracrine effects of these cells through the release of pro-angiogenic growth and survival factors. Moreover, hematopoietic stem cells characterized by CD133+ and/or CD34+ expression might contribute directly or indirectly to cardiac remodeling, myocyte survival, or long-term improvements in contractile function.

Patel et al. reported a randomized, double-blind, placebo-controlled phase 2B trial (ixCELL-DCM), to which patients from 31 sites in North America with New York Heart Association class III or IV symptomatic heart failure due to ischemic dilated cardiomyopathy, who had left ventricular ejection fraction 35% or less, an automatic implantable cardioverter defibrillator, and who were ineligible for revascularization procedures were randomly assigned (1:1) to receive ixmyelocel-T or placebo at the time of bone marrow aspiration and followed for 12 months. Randomization was done through an interactive (voice/web) response system. The pharmacist, treating physician, and coordinator at each site were unblinded, but the follow-up team was completely blinded. The primary endpoint was a composite of all-cause death, cardiovascular admission to hospital, and unplanned clinic visits to treat acute decompensated heart failure based on the blinded adjudication of an independent clinical endpoint committee. Primary efficacy endpoint analyses and safety analyses were done by modified intention to treat. 126 participants were randomly assigned to receive either ixmyelocel-T (n=66) or placebo (n=60). One-hundred and fourteen (90%) patients comprised the modified intention-to-treat population and 109 (87%) patients were included in the per-protocol primary efficacy analysis (58 in the ixmyelocel-T group and 51 in the placebo group). The primary efficacy endpoint was observed in 47 patients: 50 events in 25 (49%) of 51 patients in the placebo group and 38 events in 22 (38%) of 58 patients in the ixmyelocel-T group, which represents a 37% reduction in cardiac events compared with placebo (risk ratio 0.63 [95% CI 0.42-0.97]; p=0.0344). Forty-one (75%) of 51 participants in the placebo group had serious adverse events versus 31 (53%) of 58 in the ixmyelocel-T group (p=0.0197). To the best of our knowledge, ixCELL-DCM is the largest cell therapy study done so far in patients with heart failure. The transendocardial delivery of ixmyelocel-T in patients with heart failure and reduced ejection fraction due to ischemic dilated cardiomyopathy resulted in a significant reduction in adjudicated clinical cardiac events compared with placebo, leading to improved patient outcomes [210].

Assessment of efficacy of autologous MSCs was made in 10 patients with chronic myocardial ischemia, left ventricular (LV) ejection fractions (EFs) of ≤35%, and reversible perfusion defects who were on stable optimal medical therapy and were not candidates for revascularization. MSCs (mean: 61.5×10(6) cells per patient) were injected into 10-16 viable sites at the border of the LV scar via a NOGA-guided catheter. Both primary endpoints, feasibility (successful harvest, expansion, and injection of autologous MSCs) and safety (absence of severe adverse events [SAEs]), were met in all 10 patients at the 1-month follow-up time point, and none of the SAEs reported during the full 2-year follow-up period was attributable to the study intervention. The results of secondary efficacy endpoint analyses identified significant improvements from baseline to Month 12 in LVEF (29.4±2.0% versus 35.7±2.5%; p=0.003), LV end-systolic volume (167.8±18.8 mL versus 156.1±28.6 mL; p=0.04), 6-min walk test, and NYHA functional class. The results suggest that autologous MSCs can be safely administered to the hearts of patients with severe, chronic, reversible myocardial ischemia and impaired cardiac function and may be associated with improvements in cardiac performance, LV remodeling, and patient functional status. A randomized, double-blind, multicenter, placebo-controlled clinical trial (MESAMI 2) will evaluate the efficacy of this treatment approach in a larger patient population [211].

In another study, a randomized, double-blind, placebo-controlled trial design was used in which patients were randomized 2:1 to intra-myocardial injections of autologous bone marrow-derived MSCs or placebo, respectively. The primary endpoint was change in left ventricular end-systolic volume (LVESV), measured by magnetic resonance imaging or computed tomography at 6 months follow-up. Sixty patients aged 30-80 years with severe ischemic heart failure, New York Heart Association (NYHA) classes II-III, left ventricular ejection fraction (LVEF)<45%, and no further treatment options were randomized. Fifty-five patients completed the 6-month follow-up (37 MSCs vs. 18 placebo). At 6 months, LVESV was reduced in the MSC group: −7.6 (95% CI −11.8 to −3.4) mL (P=0.001), and increased in the placebo group: 5.4 (95% CI −0.4 to 11.2) mL (P=0.07). The difference between groups was 13.0 (95% CI 5.9-20.1) mL (P=0.001). Compared with placebo, there were also significant improvements in LVEF of 6.2% (P<0.0001), stroke volume of 18.4 mL (P<0.0001), and myocardial mass of 5.7 g (P=0.001). No differences were found in NYHA class, 6-min walking test and Kansas City cardiomyopathy questionnaire. No side effects were identified. The authors concluded that intra-myocardial injections of autologous culture-expanded MSCs were safe and improved myocardial function in patients with severe ischemic heart failure [212].

Combination of autologous bone marrow MSCs together with the CABG procedure was assessed in the PROMETHEUS trial. Six patients were injected with autologous MSCs into akinetic/hypokinetic myocardial territories not receiving bypass graft for clinical reasons. MRI was used to measure scar, perfusion, wall thickness, and contractility at baseline at 3, 6, and 18 months and to compare structural and functional recovery in regions that received MSC injections alone, revascularization alone, or neither. A composite score of MRI variables was used to assess concordance of antifibrotic effects, perfusion, and contraction at different regions. After 18 months, subjects receiving MSCs exhibited increased LV ejection fraction (+9.4±1.7%, P=0.0002) and decreased scar mass (−47.5±8.1%; P<0.0001) compared with baseline. MSC-injected segments had concordant reduction in scar size, perfusion, and contractile improvement (concordant score: 2.93±0.07), whereas revascularized (0.5±0.21) and nontreated segments (−0.07±0.34) demonstrated nonconcordant changes (P<0.0001 versus injected segments). The authors concluded that intramyocardial injection of autologous MSCs into akinetic yet nonrevascularized segments produces comprehensive regional functional restitution, which in turn drives improvement in global LV function [213].

Another study examined effects of administration of autologous BM-MSCs during CABG procedure in 30 patients. Specifically, 15 patients (all men, average age 57) formed the test arm who underwent CABG plus Bone Marrow Mesenchymal Stem Cell (BM-MSC) transplantation, whereas another 15 patients who underwent conventional CABG only (14 men and 1 woman, mean age 57) served as the control arm. The cell transplantation consisted of injecting BM-MSCs in the border zone of the clearly visible infarcted area transepicardially. The absolute number of MSCs injected ranged between 3 million and 26 million cells. The data for change from baseline in the area of infarct was collected at 3 months and 6 months during the study and analyzed using paired t-tests. The mean percentage perfusion improvement from baseline in the area of infarct supplied by the Left Anterior Descending Artery (LAD) was higher in the cases (35.8%) as compared to the controls (11.3%) at 3 months post treatment (p value <0.05). There were three cases of arrhythmia, and none of the adverse events recorded was due to the investigational product. Improvement in the ejection fraction was similar in the cases and controls [214].

Josh Hare's group reported a phase 1 and 2 randomized, blinded, placebo-controlled study involving 65 patients with ischemic cardiomyopathy and left ventricular (LV) ejection fraction less than 50% (Sep. 1, 2009-Jul. 12, 2013). The study compared injection of MSCs (n=19) with placebo (n=11) and BMCs (n=19) with placebo (n=10), with 1 year of follow-up. Injections were given in 10 LV sites with an infusion catheter. No patients had treatment-emergent serious adverse events at day 30. The 1-year incidence of serious adverse events was 31.6% (95% CI, 12.6% to 56.6%) for MSCs, 31.6% (95% CI, 12.6%-56.6%) for BMCs, and 38.1% (95% CI, 18.1%-61.6%) for placebo. Over 1 year, the Minnesota Living with Heart Failure score improved with MSCs (−6.3; 95% CI, −15.0 to 2.4; repeated measures of variance, P=0.02) and with BMCs (−8.2; 95% CI, −17.4 to 0.97; P=0.005) but not with placebo (0.4; 95% CI, −9.45 to 10.25; P=0.38). The 6-minute walk distance increased with MSCs only (repeated measures model, P=0.03). Infarct size as a percentage of LV mass was reduced by MSCs (−18.9%; 95% CI, −30.4 to −7.4; within-group, P=0.004) but not by BMCs (−7.0%; 95% CI, −15.7% to 1.7%; within-group, P=0.11) or placebo (−5.2%; 95% CI, −16.8% to 6.5%; within-group, P=0.36). Regional myocardial function as peak Eulerian circumferential strain at the site of injection improved with MSCs (−4.9; 95% CI, −13.3 to 3.5; within-group repeated measures, P=0.03) but not BMCs (−2.1; 95% CI, −5.5 to 1.3; P=0.21) or placebo (−0.03; 95% CI, −1.9 to 1.9; P=0.14). Left ventricular chamber volume and ejection fraction did not change. The authors concluded that transendocardial stem cell injection with MSCs or BMCs appeared to be safe for patients with chronic ischemic cardiomyopathy and LV dysfunction. Although the sample size and multiple comparisons preclude a definitive statement about safety and clinical effect, these results provide the basis for larger studies to provide definitive evidence about safety and to assess efficacy of this new therapeutic approach [215].

Transendocardial stem cell injection (TESI) with mesenchymal stem cells improves remodeling in chronic ischemic cardiomyopathy, but the effect of the injection site remains unknown. In order to address whether TESI exerts its effects at the site of injection only or also in remote areas, we hypothesized that segmental myocardial scar and segmental ejection fraction improve to a greater extent in injected than in noninjected segments. Biplane ventriculographic and endocardial tracings were recorded. TESI was guided to 10 sites in infarct border zones. Sites were mapped according to the 17 myocardial segment model. As a result, 510 segments were analyzed in 30 patients before and 13 months after TESI. Segmental early enhancement defect (a measure of scar size) was reduced by TESI in both injected (−43.7±4.4%; n=95; P<0.01) and noninjected segments (−25.1±7.8%; n=148; P<0.001; between-group comparison P<0.05). Conversely, segmental ejection fraction (a measure of contractile performance) improved in injected scar segments (19.9±3.3-26.3±3.5%; P=0.003) but not in noninjected scar segments (21.3±2.6-23.5±3.2%; P=0.20; between-group comparison P<0.05). Furthermore, segmental ejection fraction in injected scar segments improved to a greater degree in patients with baseline segmental ejection fraction <20% (12.1±1.2-19.9±2.7%; n=18; P=0.003), versus <20% (31.7±3.4-35.5±3.3%; n=12; P=0.33, between-group comparison P<0.0001). The authors concluded that a dichotomy exists in regional responses to TESI. Although scar size reduction was evident in all scar segments, scar size reduction and ventricular functional responses preferentially occurred at the sites of TESI versus non-TESI sites. Furthermore, improvement was greatest when segmental left ventricular dysfunction was severe [216].

In a 3-year follow up study, 31 patients with severe stable CAD and refractory angina were included. Patients had reversible myocardial ischemia and no further revascularization options. Autologous BM-MSCs were isolated, culture expanded and stimulated with vascular endothelial growth factor to facilitate endothelial differentiation. BM-MSCs were injected into an ischemic, viable region of the myocardium. The investigators found significant clinical improvements in exercise time (p=0.0016), angina class (CCS) (p<0.0001), weekly number of angina attacks (p<0.0001), and use of nitroglycerin from (p=0.0017). In the Seattle Angina Questionnaire there were significant improvements in physical limitation score, angina stability score, angina frequency score, and quality of life score (all p<0.0001). When comparing all hospital admissions from 3 years before to 3 years after treatment, they observed highly reduced admission rates for stable angina (p<0.0001), revascularization (p=0.003) and overall cardiovascular disease (p<0.0001). No early or late side effects of the treatment were observed [217].

One attempt to increase efficacy of autologous BM-MSCs by differentiating them in vitro toward the cardiac lineage before implantation was performed during the C-CURE (Cardiopoietic stem Cell therapy in heart failURE) trial, a prospective, multicenter, randomized trial conducted in patients with heart failure of ischemic origin who received standard of care or standard of care plus lineage-specified stem cells. In the cell therapy arm, bone marrow was harvested and isolated mesenchymal stem cells were exposed to a cardiogenic cocktail. Derived cardiopoietic stem cells, meeting release criteria under Good Manufacturing Practice, were delivered by endomyocardial injections guided by left ventricular electromechanical mapping. Data acquisition and analysis were performed in blinded fashion. The primary endpoint was feasibility/safety at 2-year follow-up. Secondary endpoints included cardiac structure/function and measures of global clinical performance 6 months post therapy. Mesenchymal stem cell cocktail-based priming was achieved for each patient with the dose attained in 75% and delivery without complications in 100% of cases. There was no evidence of increased cardiac or systemic toxicity induced by cardiopoietic cell therapy. Left ventricular ejection fraction was improved by cell therapy (from 27.5±1.0% to 34.5±1.1%) versus standard of care alone (from 27.8±2.0% to 28.0±1.8%, p<0.0001) and was associated with a reduction in left ventricular end-systolic volume (−24.8±3.0 ml vs. −8.8±3.9 ml, p<0.001). Cell therapy also improved the 6-min walk distance (+62±18 m vs. −15±20 m, p<0.01) and provided a superior composite clinical score encompassing cardiac parameters in tandem with New York Heart Association functional class, quality of life, physical performance, hospitalization, and event-free survival [218].

Another attempt to increase efficacy of autologous MSCs was performed using culture in the angiogenic cytokine VEGF. A total of 31 patients with stable CAD, moderate to severe angina, normal left ventricular ejection fraction, and no further revascularization options were included. Bone marrow MSCs were isolated and culture expanded for 6-8 weeks and then stimulated with vascular endothelial growth factor (VEGF) for 1 week. The 12-month follow-up demonstrated that it was safe to culture expand MSCs and use the cells for clinical treatment. The patients' maximal metabolic equivalent (MET) during exercise increased from 4.23 MET at baseline to 4.72 MET at 12-month follow-up (p<0.001), Canadian Cardiovascular Society Class (CCS) was reduced from 3.0 to 0.8 (p<0.001), angina attacks per week were reduced from 13.8 to 3.2 (p<0.001), and nitroglycerin consumption from 10.7 to 3.4 per week (p<0.001). In addition, Seattle Angina Questionnaire (SAQ) evaluations demonstrated highly significant improvements in physical limitation, angina stability, angina frequency, and quality of life (p<0.001 for all). It is safe in the intermediate/long term to treat patients with stable CAD using autologous culture expanded MSCs. Previously reported, early and highly significant improvements in exercise capacity and clinical symptoms persist after 12 months [219].

A study examined the effects of autologous MSCs in dilated cardiomyopathy (DCM). Ten symptomatic patients with DCM and refractory cardiac function, despite maximum medical therapy, were selected. Five had ischemic DCM deemed unlikely to benefit from revascularization alone and underwent bypass operations with concurrent intramyocardial MSC injection (group A). Two patients had previous revascularization and three had non-ischemic DCM and received intracoronary MSC injection (group B). Group A and B patients received 0.5-1.0×10(6) and 2.0-3.0× 10(6) MSC/kg body weight, respectively. All patients remained alive at 1 year. There were significant improvements from baseline to 6 and 12 months in left ventricular ejection fraction and other left ventricular parameters. Scar reduction was noted in six patients by 12 months [220]. Another study examined reverse remodeling induced by MSC treatment. Eight patients (aged 57.2±13.3 years) received transendocardial, intramyocardial injection of autologous bone marrow progenitor cells (mononuclear or mesenchymal stem cells) in LV scar and border zone. All patients tolerated the procedure with no serious adverse events. CMR at 1 year demonstrated a decrease in end-diastolic volume (208.7±20.4 versus 167.4±7.32 mL; P=0.03), a trend toward decreased end-systolic volume (142.4±16.5 versus 107.6±7.4 mL; P=0.06), decreased infarct size (P<0.05), and improved regional LV function by peak Eulerian circumferential strain in the treated infarct zone (−8.1±1.0 versus −11.4±1.3; P=0.04). Improvements in regional function were evident at 3 months, whereas the changes in chamber dimensions were not significant until 6 months. Improved regional function in the infarct zone strongly correlated with reduction of end-diastolic volume (r(2)=0.69, P=0.04) and end-systolic volume (r(2)=0.83, P=0.01) [221].

A case report involving intracoronary injection of autologous bone marrow-derived mesenchymal stem cells in a boy with progressive dilated cardiomyopathy stated that the practice is feasible and safe. Furthermore, it provided positively influenced functional class, quality of life and echocardiographic indices of cardiac function by administration of autologous BMMSCs [222]. A larger combination cell trial was performed in which ten patients with stable angina pectoris (class III to IV) on maximal medical therapy were included. All patients had ≥70% stenosis in at least one coronary artery, and none was considered a candidate for percutaneous coronary intervention or coronary artery bypass graft. Endpoints were feasibility and safety of intracoronary infusion of the combination cell product and assessment of myocardial ischemia, left ventricular ejection fraction (LVEF), and quality of life at 6 months post infusion. Six months after cell infusion there were no adverse clinical events. Functional cardiac evaluation during the same period showed significant improvements in LVEF (average increase: 11%, P=0.02) and myocardial ischemia (average decrease: 1.8 fold, P=0.02). Additionally, all patients described significant improvements in quality of life [223].

The phase IIA safety study was designed to enroll 11 patients who were treated with allogeneic mesenchymal precursor cells during CAB G. Preoperative scintigraphy imaging (SPECT) was used to identify hibernating myocardium not suitable for conventional myocardial revascularization for iMP implantation. iMP cells were implanted intramyocardially in predefined viable peri-infarct areas that showed poor perfusion, which could not be grafted due to poor target vessel quality. Postoperatively, SPECT was then used to identify changes in scar area. Intramyocardial implantation of iMP cells with CABG was safe with preliminary evidence of efficacy of improved myocardial contractility and perfusion of nonrevascularized territories, resulting in a significant reduction in left ventricular scar area at 12 months after treatment. Clinical improvement was associated with a significant improvement in quality of life at 6 months post treatment in all patients. The results suggest the potential for in situ myocardial regeneration in ischemic heart failure by delivery of iMP cells [224].

Using Mesoblast's Mesenchymal Precursor Cell (MPC)-type of bone marrow MSC, 60 patients were sequentially allocated to a dosing cohort (20 per dose group) and randomized them to transendocardial MPC injections (n=15) or mock procedures (n=5). The primary objective was safety, including antibody testing. Secondary efficacy endpoints included major adverse cardiac events (MACE: cardiac death, myocardial infarction, or revascularization), left ventricular imaging, and other clinical event surrogates. Safety and MACE were evaluated for up to 3 years. MPC injections were feasible and safe. Adverse events were similar across groups. No clinically symptomatic immune responses were noted. MACE was seen in 15 patients: 10 of 45 (22%) MPC-treated and 5 of 15 (33%) control patients. Study authors found no differences between MPC-treated and control patients in survival probability, MACE-free probability, and all-cause mortality. They conducted a post hoc analysis of HF-related MACE (HF hospitalization, successfully resuscitated cardiac death, or cardiac death) and events were significantly reduced in the 150 million MPC group (0/15) versus control (5/15; 33%), 25 million MPC group (3/15; 20%), and 75 million MPC group (6/15; 40%); the 150 million MPC group differed significantly from all groups according to Kaplan-Meier statistics >3 years (P=0.025 for 150 million MPC group versus control) [225].

One of the reasons for using allogeneic MSCs is that they do not suffer from inherent deficiencies that are found when autologous MSCs are used from patients suffering from chronic disease. In an interesting study a comparison was made between allogeneic and autologous MSCs in patients with idiopathic dilated and ischemic cardiomyopathy. Patients were randomly assigned to receive autologous (n=7) or allogeneic (n=15) MSCs. The authors assessed EPC-colony forming units (EPC-CFUs), FMD, and circulating levels of vascular endothelial growth factor (VEGF) in patients before and three months after MSC transendocardial injection (n=22) and in healthy controls (n=10). EPC-CFUs were markedly reduced in HF compared to healthy controls (4±3 vs. 25±16 CFUs, P<0.0001). Similarly, FMD % was impaired in HF (5.6±3.2% vs. 9.0±3.3%, P=0.01). Allogeneic, but not autologous, MSCs improved endothelial function three months after treatment (Δ10±5 vs. 41±3 CFUs, P=0.0067; 43.7±3% vs. 4-0.46±3% FMD, P=0.005). Patients who received allogeneic MSCs had a reduction in serum VEGF levels three months after treatment, while patients who received autologous MSCs had an increase (P=0.0012), and these changes correlated with the change in EPC-CFUs (P<0.0001). Lastly, human umbilical vein endothelial cells (HUVECs) with impaired vasculogenesis due to pharmacologic nitric oxide synthase inhibition were rescued by allogeneic MSC-conditioned medium (P=0.006). The authors concluded that a novel mechanism exists whereby allogeneic, but not autologous, MSC administration results in the proliferation of functional EPCs and improvement in vascular reactivity, which in turn restores endothelial function toward normal in patients with HF [226].

Left ventricle assist devices (LVAD) are a useful bridge until patients receive a donor cardiac transplant. Some indications suggest that LVADs actually assist myocardial regeneration. In order to augment this possible effect, a multicenter, double-blind, sham procedure-controlled trial was performed in which 30 patients were randomized (2:1) to intramyocardial injection of 25 million MPCs or medium during LVAD implantation. The primary safety endpoint was incidence of infectious myocarditis, myocardial rupture, neoplasm, hypersensitivity reaction, and immune sensitization (90 days after randomization). Key efficacy endpoints were functional status and ventricular function while temporarily weaned from LVAD support (90 days after randomization). Patients were followed up until transplant or 12 months after randomization, whichever came first. Mean age was 57.4 (±13.6) years, mean left ventricular ejection fraction was 18.1%, and 66.7% were destination therapy LVADs. No safety events were observed. Successful temporary LVAD weaning was achieved in 50% of MPC and 20% of control patients at 90 days (P=0.24); the probability that MPCs increased the likelihood of successful weaning was 93%. At 90 days, 3 deaths (30%) occurred in control patients, and none occurred in MPC patients. Mean left ventricular ejection fraction after successful wean was 24.0% (MPC=10) and 22.5% (control=2; P=0.56). At 12 months, 30% of MPC patients and 40% of control patients were successfully temporarily weaned from LVAD support (P=0.69), and 6 deaths (30%) occurred in MPC patients. Donor-specific HLA sensitization developed in 2 MPC and 3 control patients and resolved by 12 months. The authors concluded that administration of MPCs appeared to be safe, and there was a potential signal of efficacy. Future studies will evaluate the potential for higher or additional doses to enhance the ability to wean LVAD recipients off support [227].

An important question in the development of cardiac therapeutics is whether autologous or allogeneic MSCs provide a superior effect. This was assessed in the POSEIDON trial. Twenty million, 100 million, or 200 million cells (5 patients in each cell type per dose level) were delivered by transendocardial stem cell injection into 10 LV sites. Within 30 days, 1 patient in each group (treatment-emergent SAE rate, 6.7%) was hospitalized for heart failure, less than the prespecified stopping event rate of 25%. The 1-year incidence of SAEs was 33.3% (n=5) in the allogeneic group and 53.3% (n=8) in the autologous group (P=0.46). At 1 year, there were no ventricular arrhythmia SAEs observed among allogeneic recipients compared with 4 patients (26.7%) in the autologous group (P=0.10). Relative to baseline, autologous but not allogeneic MSC therapy was associated with an improvement in the 6-minute walk test and the MLHFQ score, but neither improved exercise VO2 max. Allogeneic and autologous MSCs reduced mean EED by −33.21% (95% CI, −43.61% to −22.81%; P<0.001) and sphericity index but did not increase EF. Allogeneic MSCs reduced LV end-diastolic volumes. Low-dose concentration MSCs (20 million cells) produced greatest reductions in LV volumes and increased EF. Allogeneic MSCs did not stimulate significant donor-specific alloimmune reactions [228].

Fifty-nine hospitalized patients with heart failure were randomly divided into a treatment group (30 patients) and a control group (29 patients). The treatment group received treatment with medication as well as intracoronary transplantation of umbilical cord MSCs, and the control group, only medication. The cardiac structure, function change, and rehospitalization and mortality rates of the 2 groups were observed before and 1 and 6 months after treatment. One month after the transplantation of umbilical cord MSCs, the incidence of fatigue, chest tightness, and dyspnea was high in the treatment group. The 6-min walking distance of the treatment group was found to be significantly higher than that of the control group (P<0.05); in addition, the NT-proBNP level, left ventricular ejection fraction, and mortality rate of the treatment group were statistically lower than those of the control group (P<0.05). Readmission rates showed a downward trend, but the difference was not statistically significant (P >0.05). The authors concluded that using umbilical cord MSCs in the treatment of congestive heart failure can help improve cardiac remodeling and cardiac function and reduce the mortality rate [229].

A study was performed to investigate the safety and feasibility of intracoronary injection of human umbilical cord mesenchymal stem cells to the very old patients with coronary chronic total occlusion. Fifteen consecutive patients received mesenchymal stem cells from human umbilical cord in epicardial coronary artery supplying collateral circulation. The patients were randomly allocated to low-dose $3\times10(6)$, mid-dose $4\times10(6)$ and high-dose $5\times10(6)$ groups. (99m)Tc single-photon emission computed tomography images were obtained at 12 and 24 months. During the 24-month study period, no cases of major cardiac adverse events were reported. None of the patients had coronary care unit hospitalizations, further coronary revascularization, acute myocardial infarction, or death. The patients had a significant reduction of the infarct size and a remarkable rise in left ventricular ejection fraction with respect to secondary outcomes. This study suggested that stem cell transplantation was safe and feasible. The cells can be utilized to improve in the degree of ischemic myocardium, decrease infarct size, and raise left ventricular ejection fraction [230]. It is interesting in that a case report supported the combination of allogeneic MSCs together with CD34 cells for enhanced synergy [231]. Yet another case report demonstrated efficacy of such a combination in a patient with dilated cardiomyopathy [232].

Lee et al. described a randomized pilot study to investigate the safety and efficacy of MSCs in patients with AMI. Eighty patients with AMI after successful reperfusion therapy were randomly assigned and received an intracoronary administration of autologous BM-derived MSCs into the infarct-related artery at 1 month. During follow-up period, 58 patients completed the trial. The primary endpoint was changes in left ventricular ejection fraction (LVEF) by single-photon emission computed tomography (SPECT) at 6 months. They also evaluated treatment-related adverse events. The absolute improvement in the LVEF by SPECT at 6 months was greater in the BM-derived MSC group than in the control group (5.9%±8.5% vs. 1.6%±7.0%; P=0.037). There was no treatment-related toxicity during intracoronary administration of MSCs. No significant adverse cardiovascular events occurred during follow-up. In conclusion, the intracoronary infusion of human BM-derived MSCs at 1 month is tolerable and safe with modest improvement in LVEF at 6-month follow-up by SPECT [233].

Safety at 5 years of autologous BM-MSCs post AMI was investigated in a clinical trial of intramyocardial injection in nine patients. Periprocedural safety analysis demonstrated one transient ischemic attack. No other adverse events related to MSC treatment were observed during 5-year follow-up. Clinical events were compared to a nonrandomized control group comprising 45 matched controls. A 5-year event-free survival after MSC treatment was comparable to controls (89 vs. 91%, P=0.87). Echocardiographic imaging for evaluation of left ventricular function demonstrated improvements up to 5 years after MSC treatment. These findings were not significantly different when compared to controls. The present safety and feasibility study suggests that intramyocardial injection of MSCs in patients shortly after AMI is feasible and safe up to 5-year follow-up [234].

Another study evaluated the influence of Bone Marrow Stem Cell (BMSC) intracoronary infusion on exercise capacity, pulmonary function, heart rate recovery, and signal-averaged electrocardiogram (SAECG) in patients with AMI of anterior wall, compared to control group—from baseline in the acute phase and during 12 months follow-up. Forty-five patients were randomized 2:1 to BMSC group (n=31 pts) or to control group (n=14 pts). BMSCs were administered into infarct-related artery (IRA) at 4-6 days after primary PCI. Patients were followed up with cardiopulmonary exercise testing. The QRS duration, QT, and QTc interval were measured and SAECGs were performed to evaluate late potentials. There were no significant differences between both groups, neither at peak VO(2) (190.7±7.4 at baseline; 24.2±5.2 at 6 months; 22.2±7.4 ml/kg/min at 12 months vs. 18.4±8.2 at baseline; 22.0±7.2 at 6 months; 21.8±6.2 ml/kg/min at 12 months; BMSC vs. control group respectively; p=ns), nor VO(2) at anaerobic threshold, nor in VE/VCO(2) slope, RER, or systolic blood pressure at peak exercise at baseline and any time point of follow-up. There were no significant differences between groups concerning HR peak, HRR1, and HRR2 at any time point and no differences between QRS, QT parameters, and SAEKGs. There were no significant differences between both groups at any time point (baseline, 6, and 12 months) concerning FVC, FEV(1), and FVC/FEV(1), and % of their normal values. The authors did not find that BMSC therapy in patients with anterior wall myocardial infarction influences exercise capacity. Furthermore, they did not observe proarrhythmogenic influence as assessed with SAECG and standard ECG analysis [235].

In a double-blind, placebo-controlled, dose-ranging (0.5, 1.6, and 5 million cells/kg) safety trial of intravenous allogeneic hMSCs (Prochymal, Osiris Therapeutics, Inc., Baltimore, Maryland) in reperfused MI patients (n=53), the primary endpoint was incidence of treatment-emergent adverse events within 6 months. Ejection fraction and left ventricular volumes determined by echocardiography and magnetic resonance imaging were exploratory efficacy endpoints. Adverse event rates were similar between the hMSC-treated (5.3 per patient) and placebo-treated (7.0 per patient) groups, and renal, hepatic, and hematologic laboratory indexes were not different. Ambulatory electrocardiogram monitoring demonstrated reduced ventricular tachycardia episodes (p=0.025), and pulmonary function testing demonstrated improved forced expiratory volume in 1 s (p=0.003) in the hMSC-treated patients. Global symptom score in all patients (p=0.027) and ejection fraction in the important subset of anterior MI patients were both significantly better in hMSC versus placebo subjects. In the cardiac magnetic resonance imaging substudy, hMSC treatment, but not placebo, increased left ventricular ejection fraction and led to reverse remodeling. The authors concluded that intravenous allogeneic hMSCs are safe in patients after acute MI and provide signals of efficacy for conduct of larger trials [236].

Stempeucel® (bone marrow-derived allogeneic mesenchymal stromal cells) or placebo was administered intravenously to 40 patients who had undergone percutaneous coronary intervention for AMI. The numbers of treatment-emergent adverse events observed were 18 and 21 in the Stempeucel and placebo groups, respectively. None of the adverse events was related to Stempeucel according to the investigators and independent data safety monitoring board. There was no serious adverse event in the Stempeucel group and there were three serious adverse events in the placebo group, of which one had a fatal outcome. Ejection fraction determined by use of echocardiography showed improvement in both Stempeucel (43.06% to 47.80%) and placebo (43.44% to 45.33%) groups at 6 months (P=0.26). Perfusion scores measured by use of single-photon emission tomography and infarct volume measured by use of magnetic resonance imaging showed no significant differences between the two groups at 6 months [237].

A trial of 116 patients with acute ST elevation MI were randomly assigned to receive an intracoronary infusion of Wharton's Jelly MSCs (WJ-MSCs) or placebo into the infarct artery at five to seven days after successful reperfusion therapy. The primary endpoint of safety, the incidence of adverse events (AEs) within 18 months, was monitored and quantified. The endpoint of efficacy—the absolute changes in myocardial viability and perfusion of the infarcted region from baseline to four months, and global left ventricular ejection fraction (LVEF) from baseline to 18 months—were measured using F-18-fluorodeoxyglucose positron emission computed tomography (F-18-FDG-PET) and 99mTc-sestamibi single-photon emission computed tomography (99mTc-SPECT), and two-dimensional echocardiography, respectively. During 18 months follow-up, AE rates and laboratory tests including tumor, immune, and hematologic indexes were not different between the two groups. The absolute increase in the myocardial viability (PET) and perfusion within the infarcted territory (SPECT) was significantly greater in the WJ-MSC group [6.9±0.6% (95% CI, 5.7 to 8.2)] and [7.1±0.8% (95% CI, 5.4 to 8.8) than in the placebo group [3.3±0.7% (95% CI, 1.8 to 4.7), P<0.0001] and 3.9±0.6(95% CI, 2.8 to 5.0), P=0.002] at four months. The absolute increase in the LVEF at 18 months in the WJ-MSC group was significantly greater than that in the placebo group [7.8±0.9 (6.0 to approximately 9.7) vs. 2.8±1.2 (0.4 to approximately 5.1), P=0.001]. Concomitantly, the absolute decreases in LV end-systolic volumes and end-diastolic volumes at 18 months in the WJ-MSC group were significantly greater than those in the placebo group (P=0.0004, P=0.004, respectively). According to the study, intracoronary infusion of WJ-MSCs appeared safe and effective in patients with AMI, providing clinically relevant therapy within a favorable time window [238].

Another study using WJ-MSCs was reported in which 10 patients with large (LVEF ≤45%, CK-MB>100 U/l) AMI with successful infarct-related artery primary percutaneous coronary intervention reperfusion (TIMI ≥2) were recruited. The patients enrolled where ages 32-65 years, peak hs-troponin T 17.3±9.1 ng/ml and peak CK-MB 533±89 U/l, sustained echo LVEF reduction to 37.6±2.6%, cMRI LVEF 40.3±2.7% and infarct size 20.1±2.8%. 30×10(6). WJ-MSCs were administered (LAD/Cx/RCA in 6/3/1) per protocol at ≈5-7 days using a cell delivery-dedicated, coronary nonocclusive method. No clinical symptoms or ECG signs of myocardial ischemia occurred. There was no epicardial flow or myocardial perfusion impairment (TIMI-3 in all; cTFC 45±8 vs. 44±9, p=0.51), and no patient showed hs-troponin T elevation (0.92±0.29≤24 h before vs. 0.89±0.28≤24 h after; decrease, p=0.04). One subject experienced, 2 days after cell transfer, a transient temperature rise (38.9° C.); this was reactive to paracetamol with no sequel. No other adverse events and no significant arrhythmias (ECG Holter) occurred. Up to 12 months there was one new, non-index territory lethal AMI but no adverse events that might be attributable to WJ-MSC treatment. This study demonstrated the feasibility and procedural safety of WJ-MSC use as off-the-shelf cellular therapy in human AMI [239].

In some embodiments said regenerative cells utilized for "training" of immune cells are made to express the enzyme indolamine 2,3 deoxygenase (IDO). Induction of this enzyme may be performed by culture conditions, such as by culture in interferon gamma, or by transfection of the enzyme.

IDO is a key homeostatic regulator and plays a key role in the immune system modulating the balance between tolerance and immunity. This gene encodes indoleamine 2,3-dioxygenase (IDO)—a heme enzyme (EC=1.13.11.52) that catalyzes the first rate-limiting step in tryptophan catabolism to N-formyl-kynurenine and acts on multiple tryptophan substrates including D-tryptophan, L-tryptophan, 5-hydroxy-tryptophan, tryptamine, and serotonin.

The basic genetic information describes indoleamine 2,3-dioxygenase 1 (IDO1, IDO, INDO) as an enzyme located at Chromosome 8p12-p11 (5; 6) that active at the first step of the Tryptophan catabolism. The cloned gene structure showed that IDO contains 10 exons ad 9 introns (7; 8) producing 9 transcripts. After alternative splicing only five of the transcripts encode a protein but the other four do not make protein products. Three of the transcripts retain introns and one of them creates a nonsense code (7). Based on IDO related studies 15 phenotypes of IDO is identified, of which, twelve in cancer tumor models of lung, kidney, endometrium, intestine, two in nervous system, and one HGMD-deletion.

The specific cellular location of IDO is in the cytosol, the smooth muscle contractile fibers and stereocilium bundle. IDO is widely expressed, but there is an elevated expression in placenta, pancreas, and the pancreas islets, including dendritic cells (DCs) (9). Expression of IDO is common in antigen presenting cells (APCs), monocytes (MO), macrophages (MQs), DCs, T-cells, and some B-cells. IDO is present in APCs (10; 11), but due to magnitude of role play hierarchy and level of expression, DCs are the better choice but including MOs during establishment of three DC cell subsets, CD14+CD25+, CD14++CD25+ and CD14+CD25++ may increase the longevity and efficacy of the interventions.

IDO is strictly regulated and confined to the immune system with diverse functions based on either positive or negative stimuli. The positive stimuli are T cell tolerance induction, apoptosis and chronic inflammatory response, type 2 immune response, and interleukin-12 production (12). The negative stimuli are interleukin-10 production, activated T cell proliferation, and T cell apoptosis. Furthermore, there are more functions allocating fetus during female pregnancy; changing behavior, responding to lipopolysaccharide or multicellular organismal response to stress possible due to degradation of tryptophan, kynurenic acid biosynthetic process, cellular nitrogen compound metabolic process, small molecule metabolic process, producing kynurenine process (13; 14; 15). IDO plays a role in a variety of pathophysiological processes such as antimicrobial and antitumor defense, neuropathology, immunoregulation, and antioxidant activity (16; 17; 18; 19).

Molecular genetics data from earlier findings based on reporter assay results showed that the IDO promoter is regulated by ISRE (interferon sequence response element)-like elements and GAS-sequence at −1126 and −1083 region (20). Two cis-acting elements are ISRE1 and ISRE2. Analyses of site directed and deletion mutation with transfected cells demonstrated that introduction of point mutations at these elements decreases the IDO expression. Removing ISRE1 decreases the effects of IFNgamma induction 50 fold and deleting ISRE1 at −1126 reduced by 25 fold (3). Introducing point mutations in conserved residues at −1124 and −1122 (from T to C or G) in the ISRE consensus sequence NAGtttCA/tntttNCC of the IFNa/b inducible gene ISG4 eliminates the promoter activity by 24 fold (21).

Example 1: Treatment of Post Infarct Failure with Reprogrammed T Cells

Forty male C57B6/J mice (age 8-12 weeks, body weight 26-30 g were randomly assigned to the following 4 groups:
(1) Normal control group: mice where exposed to sham surgery and injected with 200 µl PBS intravenously 30 min later (Control).
(2) LAD infarct group: mice had myocardial infarction induced by permanent ligation of the left anterior descending coronary artery. For this, the mice (78 in total] were anesthetized using 3-4% (vol./vol.) isoflurane, intubated, and ventilated with oxygen/0.8-1.2% isoflurane.
(3) Unprogrammed T Cells: myocardial infarction was induced in mice by LAD ligation and where subsequently injected intravenously with 1×10(6) C57/B6 T cells suspended in 200 µl of PBS 30 min later.
(4) Programmed T Cells: myocardial infarction was induced in mice by LAD ligation and mice were injected intravenously with 1×106 C57/BL6 T cells that were "programmed" by culture with BALB/c bone marrow MSC. These cells were admixed at a one to one ratio with C57/BL6 T cells and cultured at 20 IU/ml interleukin 2. Concentration of T cells and BM-MSC in culture was 500,000 cells per ml. After 48 hours of culture T cells were purified by gently removing the non-adherent fraction. 1 million T cells were suspended in 200 µl of PBS and injected.

Percentage of Survival was measured on days 7, 10, and 12. Results are shown in FIG. 1.

REFERENCES

1. DeBerge, M., et al., *Monocytes prime autoreactive T cells after myocardial infarction*. Am J Physiol Heart Circ Physiol, 2020. 318(1): p. H116-H123.
2. Nestle, F. O., et al., *Vaccination of melanoma patients with peptide-or tumor lysate-pulsed dendritic cells*. Nat Med, 1998. 4(3): p. 328-32.
3. Chakraborty, N. G., et al., *Immunization with a tumor-cell-lysate-loaded autologous-antigen-presenting-cell-based vaccine in melanoma*. Cancer Immunol Immunother, 1998. 47(1): p. 58-64.
4. Wang, F., et al., *Phase I trial of a MART-1 peptide vaccine with incomplete Freund's adjuvant for resected high-risk melanoma*. Clin Cancer Res, 1999. 5(10): p. 2756-65.
5. Thurner, B., et al., *Vaccination with mage-3A1 peptide pulsed mature, monocyte-derived dendritic cells expands specific cytotoxic T cells and induces regression of some metastases in advanced stage IV melanoma*. J Exp Med, 1999. 190(11): p. 1669-78.
6. Thomas, R., et al., *Immature human monocyte-derived dendritic cells migrate rapidly to draining lymph nodes after intradermal injection for melanoma immunotherapy*. Melanoma Res, 1999. 9(5): p. 474-81.
7. Mackensen, A., et al., *Phase I study in melanoma patients of a vaccine with peptide-pulsed dendritic cells generated in vitro from CD34(+) hematopoietic progenitor cells*. Int J Cancer, 2000. 86(3): p. 385-92.
8. Panelli, M. C., et al., *Phase 1 study in patients with metastatic melanoma of immunization with dendritic cells presenting epitopes derived from the melanoma-associated antigens MART-1 and gp100*. J Immunother, 2000. 23(4): p. 487-98.
9. Schuler-Thurner, B., et al., *Mage-3 and influenza-matrix peptide-specific cytotoxic T cells are inducible in terminal stage HLA-A2.1+ melanoma patients by mature monocyte-derived dendritic cells*. J Immunol, 2000. 165(6): p. 3492-6.
10. Lau, R., et al., *Phase I trial of intravenous peptide-pulsed dendritic cells in patients with metastatic melanoma*. J Immunother, 2001. 24(1): p. 66-78.
11. Banchereau, J., et al., *Immune and clinical responses in patients with metastatic melanoma to CD34(+) progenitor-derived dendritic cell vaccine*. Cancer Res, 2001. 61(17): p. 6451-8.
12. Schuler-Thurner, B., et al., *Rapid induction of tumor-specific type 1 T helper cells in metastatic melanoma patients by vaccination with mature, cryopreserved, peptide-loaded monocyte-derived dendritic cells*. J Exp Med, 2002. 195(10): p. 1279-88.
13. Palucka, A. K., et al., *Single injection of CD34+ progenitor-derived dendritic cell vaccine can lead to induction of T-cell immunity in patients with stage IV melanoma*. J Immunother, 2003. 26(5): p. 432-9.
14. Bedrosian, I., et al., *Intranodal administration of peptide pulsed mature dendritic cell vaccines results in superior CD8+T-cell function in melanoma patients*. J Clin Oncol, 2003. 21(20): p. 3826-35.
15. Slingluff, C. L., Jr., et al., *Clinical and immunologic results of a randomized phase II trial of vaccination using four melanoma peptides either administered in granulocyte-macrophage colony-stimulating factor in adjuvant or pulsed on dendritic cells*. J Clin Oncol, 2003. 21(21): p. 4016-26.
16. Hersey, P., et al., *Phase I/II study of treatment with dendritic cell vaccines in patients with disseminated melanoma*. Cancer Immunol Immunother, 2004. 53(2): p. 125-34.
17. Vilella, R., et al., *Pilot study of treatment of biochemotherapy-refractory stage IV melanoma patients with autologous dendritic cells pulsed with a heterologous melanoma cell line lysate*. Cancer Immunol Immunother, 2004. 53(7): p. 651-8.
18. Palucka, A. K., et al., *Spontaneous proliferation and type 2 cytokine secretion by CD4+T cells in patients with metastatic melanoma vaccinated with antigen-pulsed dendritic cells*. J Clin Immunol, 2005. 25(3): p. 288-95.
19. Banchereau, J., et al., *Immune and clinical outcomes in patients with stage IV melanoma vaccinated with peptide-pulsed dendritic cells derived from CD34+ progenitors and activated with type I interferon*. J Immunother, 2005. 28(5): p. 505-16.
20. Trakatelli, M., et al., *A new dendritic cell vaccine generated with interleukin-3 and interferon-beta induces*

*CD8+ T cell responses against NA17-A2 tumor peptide in melanoma patients.* Cancer Immunol Immunother, 2006. 55(4): p. 469-74.
21. Salcedo, M., et al., *Vaccination of melanoma patients using dendritic cells loaded with an allogeneic tumor cell lysate.* Cancer Immunol Immunother, 2006. 55(7): p. 819-29.
22. Linette, G. P., et al., *Immunization using autologous dendritic cells pulsed with the melanoma-associated antigen gp100-derived G280-9V peptide elicits CD8+ immunity.* Clin Cancer Res, 2005. 11(21): p. 7692-9.
23. Escobar, A., et al., *Dendritic cell immunizations alone or combined with low doses of interleukin-2 induce specific immune responses in melanoma patients.* Clin Exp Immunol, 2005. 142(3): p. 555-68.
24. Tuettenberg, A., et al., *Induction of strong and persistent MelanA/MART-1-specific immune responses by adjuvant dendritic cell-based vaccination of stage II melanoma patients.* Int J Cancer, 2006. 118(10): p. 2617-27.
25. Schadendorf, D., et al., *Dacarbazine (DTIC) versus vaccination with autologous peptide— pulsed dendritic cells (DC) in first-line treatment of patients with metastatic melanoma: a randomized phase III trial of the DC study group of the DeCOG.* Ann Oncol, 2006. 17(4): p. 563-70.
26. Di Pucchio, T., et al., *Immunization of stage IV melanoma patients with Melan-A/MART-1 and gp100 peptides plus IFN-alpha results in the activation of specific CD8(+) T cells and monocyte/dendritic cell precursors.* Cancer Res, 2006. 66(9): p. 4943-51.
27. Nakai, N., et al., *Vaccination of Japanese patients with advanced melanoma with peptide, tumor lysate or both peptide and tumor lysate pulsed mature, monocyte-derived dendritic cells.* J Dermatol, 2006. 33(7): p. 462-72.
28. Palucka, A. K., et al., *Dendritic cells loaded with killed allogeneic melanoma cells can induce objective clinical responses and MART-1 specific CD8+ T-cell immunity.* J Immunother, 2006. 29(5): p. 545-57.
29. Lesimple, T., et al., *Immunologic and clinical effects of injecting mature peptide-loaded dendritic cells by intralymphatic and intranodal routes in metastatic melanoma patients.* Clin Cancer Res, 2006. 12(24): p. 7380-8.
30. Guo, J., et al., *Intratumoral injection of dendritic cells in combination with local hyperthermia induces systemic antitumor effect in patients with advanced melanoma.* Int J Cancer, 2007. 120(11): p. 2418-25.
31. O'Rourke, M. G., et al., *Dendritic cell immunotherapy for stage IV melanoma.* Melanoma Res, 2007. 17(5): p. 316-22.
32. Bercovici, N., et al., *Analysis and characterization of antitumor T-cell response after administration of dendritic cells loaded with allogeneic tumor lysate to metastatic melanoma patients.* J Immunother, 2008. 31(1): p. 101-12.
33. Hersey, P., et al., *Phase I/II study of treatment with matured dendritic cells with or without low dose IL-2 in patients with disseminated melanoma.* Cancer Immunol Immunother, 2008. 57(7): p. 1039-51.
34. von Euw, E. M., et al., *A phase I clinical study of vaccination of melanoma patients with dendritic cells loaded with allogeneic apoptotic/necrotic melanoma cells. Analysis of toxicity and immune response to the vaccine and of IL-10-1082 promoter genotype as predictor of disease progression.* J Transl Med, 2008. 6: p. 6.
35. Carrasco, J., et al., *Vaccination of a melanoma patient with mature dendritic cells pulsed with MAGE-3 peptides triggers the activity of nonvaccine anti-tumor cells.* J Immunol, 2008. 180(5): p. 3585-93.
36. Redman, B. G., et al., *Phase Ib trial assessing autologous, tumor-pulsed dendritic cells as a vaccine administered with or without IL-2 in patients with metastatic melanoma.* J Immunother, 2008. 31(6): p. 591-8.
37. Daud, A. I., et al., *Phenotypic and functional analysis of dendritic cells and clinical outcome in patients with high-risk melanoma treated with adjuvant granulocyte macrophage colony-stimulating factor.* J Clin Oncol, 2008. 26(19): p. 3235-41.
38. Engell-Noerregaard, L., et al., *Review of clinical studies on dendritic cell-based vaccination of patients with malignant melanoma: assessment of correlation between clinical response and vaccine parameters.* Cancer Immunol Immunother, 2009. 58(1): p. 1-14.
39. Nakai, N., et al., *Immunohistological analysis of peptide-induced delayed-type hypersensitivity in advanced melanoma patients treated with melanoma antigen pulsed mature monocyte-derived dendritic cell vaccination.* J Dermatol Sci, 2009. 53(1): p. 40-7.
40. Dillman, R. O., et al., *Phase II trial of dendritic cells loaded with antigens from self-renewing, proliferating autologous tumor cells as patient-specific antitumor vaccines in patients with metastatic melanoma: final report.* Cancer Biother Radiopharm, 2009. 24(3): p. 311-9.
41. Chang, J. W., et al., *Immunotherapy with dendritic cells pulsed by autologous dactinomycin-induced melanoma apoptotic bodies for patients with malignant melanoma.* Melanoma Res, 2009. 19(5): p. 309-15.
42. Trepiakas, R., et al., *Vaccination with autologous dendritic cells pulsed with multiple tumor antigens for treatment of patients with malignant melanoma: results from a phase I/II trial.* Cytotherapy, 2010. 12(6): p. 721-34.
43. Jacobs, J. F., et al., *Dendritic cell vaccination in combination with anti-CD25 monoclonal antibody treatment: a phase I/II study in metastatic melanoma patients.* Clin Cancer Res, 2010. 16(20): p. 5067-78.
44. Ribas, A., et al., *Multicenter phase II study of matured dendritic cells pulsed with melanoma cell line lysates in patients with advanced melanoma.* J Transl Med, 2010. 8: p. 89.
45. Ridolfi, L., et al., *Unexpected high response rate to traditional therapy after dendritic cell-based vaccine in advanced melanoma: update of clinical outcome and subgroup analysis.* Clin Dev Immunol, 2010. 2010: p. 504979.
46. Cornforth, A. N., et al., *Resistance to the proapoptotic effects of interferon-gamma on melanoma cells used in patient-specific dendritic cell immunotherapy is associated with improved overall survival.* Cancer Immunol Immunother, 2011. 60(1): p. 123-31.
47. Lesterhuis, W. J., et al., *Wild-type and modified gp100 peptide-pulsed dendritic cell vaccination of advanced melanoma patients can lead to long-term clinical responses independent of the peptide used.* Cancer Immunol Immunother, 2011. 60(2): p. 249-60.
48. Bjoern, J., et al., *Changes in peripheral blood level of regulatory T cells in patients with malignant melanoma during treatment with dendritic cell vaccination and low-dose IL-2.* Scand J Immunol, 2011. 73(3): p. 222-33.
49. Steele, J. C., et al., *Phase I/II trial of a dendritic cell vaccine transfected with DNA encoding melan A and gp100 for patients with metastatic melanoma.* Gene Ther, 2011. 18(6): p. 584-93.

50. Kim, D. S., et al., *Immunotherapy of malignant melanoma with tumor lysate-pulsed autologous monocyte-derived dendritic cells*. Yonsei Med J, 2011. 52(6): p. 990-8.
51. Ellebaek, E., et al., *Metastatic melanoma patients treated with dendritic cell vaccination, Interleukin-2 and metronomic cyclophosphamide: results from a phase II trial*. Cancer Immunol Immunother, 2012. 61(10): p. 1791-804.
52. Dillman, R. O., et al., *Tumor stem cell antigens as consolidative active specific immunotherapy: a randomized phase II trial of dendritic cells versus tumor cells in patients with metastatic melanoma*. J Immunother, 2012. 35(8): p. 641-9.
53. Dannull, J., et al., *Melanoma immunotherapy using mature DCs expressing the constitutive proteasome*. J Clin Invest, 2013. 123(7): p. 3135-45.
54. Finkelstein, S. E., et al., *Combination of external beam radiotherapy (EBRT) with intratumoral injection of dendritic cells as neo-adjuvant treatment of high-risk soft tissue sarcoma patients*. Int J Radiat Oncol Biol Phys, 2012. 82(2): p. 924-32.
55. Stift, A., et al., *Dendritic cell vaccination in medullary thyroid carcinoma*. Clin Cancer Res, 2004. 10(9): p. 2944-53.
56. Kuwabara, K., et al., *Results of a phase I clinical study using dendritic cell vaccinations for thyroid cancer*. Thyroid, 2007. 17(1): p. 53-8.
57. Bachleitner-Hofmann, T., et al., *Pilot trial of autologous dendritic cells loaded with tumor lysate(s) from allogeneic tumor cell lines in patients with metastatic medullary thyroid carcinoma*. Oncol Rep, 2009. 21(6): p. 1585-92.
58. Yu, J. S., et al., *Vaccination of malignant glioma patients with peptide-pulsed dendritic cells elicits systemic cytotoxicity and intracranial T-cell infiltration*. Cancer Res, 2001. 61(3): p. 842-7.
59. Yamanaka, R., et al., *Vaccination of recurrent glioma patients with tumour lysate pulsed dendritic cells elicits immune responses: results of a clinical phase I/II trial*. Br J Cancer, 2003. 89(7): p. 1172-9.
60. Yu, J. S., et al., *Vaccination with tumor lysate-pulsed dendritic cells elicits antigen— specific, cytotoxic T-cells in patients with malignant glioma*. Cancer Res, 2004. 64(14): p. 4973-9.
61. Yamanaka, R., et al., *Tumor lysate and IL-18 loaded dendritic cells elicits Th1 response, tumor-specific CD8+ cytotoxic T cells in patients with malignant glioma*. J Neurooncol, 2005. 72(2): p. 107-13.
62. Yamanaka, R., et al., *Clinical evaluation of dendritic cell vaccination for patients with recurrent glioma: results of a clinical phase I/II trial*. Clin Cancer Res, 2005. 11(11): p. 4160-7.
63. Liau, L. M., et al., *Dendritic cell vaccination in glioblastoma patients induces systemic and intracranial T-cell responses modulated by the local central nervous system tumor microenvironment*. Clin Cancer Res, 2005. 11(15): p. 5515-25.
64. Walker, D. G., et al., *Results of a phase I dendritic cell vaccine trial for malignant astrocytoma: potential interaction with adjuvant chemotherapy*. J Clin Neurosci, 2008. 15(2): p. 114-21.
65. Leplina, O. Y., et al., *Use of interferon-alpha-induced dendritic cells in the therapy of patients with malignant brain gliomas*. Bull Exp Biol Med, 2007. 143(4): p. 528-34.
66. De Vleeschouwer, S., et al., *Postoperative adjuvant dendritic cell-based immunotherapy in patients with relapsed glioblastoma multiforme*. Clin Cancer Res, 2008. 14(10): p. 3098-104.
67. Ardon, H., et al., *Adjuvant dendritic cell-based tumour vaccination for children with malignant brain tumours*. Pediatr Blood Cancer, 2010. 54(4): p. 519-25.
68. Prins, R. M., et al., *Gene expression profile correlates with T-cell infiltration and relative survival in glioblastoma patients vaccinated with dendritic cell immunotherapy*. Clin Cancer Res, 2011. 17(6): p. 1603-15.
69. Okada, H., et al., *Induction of CD8+T-cell responses against novel glioma-associated antigen peptides and clinical activity by vaccinations with [alpha]-type 1 polarized dendritic cells and polyinosinic-polycytidylic acid stabilized by lysine and carboxymethylcellulose in patients with recurrent malignant glioma*. J Clin Oncol, 2011. 29(3): p. 330-6.
70. Fadul, C. E., et al., *Immune response in patients with newly diagnosed glioblastoma multiforme treated with intranodal autologous tumor lysate-dendritic cell vaccination after radiation chemotherapy*. J Immunother, 2011. 34(4): p. 382-9.
71. Chang, C. N., et al., *A phase I/II clinical trial investigating the adverse and therapeutic effects of a postoperative autologous dendritic cell tumor vaccine in patients with malignant glioma*. J Clin Neurosci, 2011. 18(8): p. 1048-54.
72. Cho, D. Y., et al., *Adjuvant immunotherapy with whole-cell lysate dendritic cells vaccine for glioblastoma multiforme: a phase II clinical trial*. World Neurosurg, 2012. 77(5-6): p. 736-44.
73. Iwami, K., et al., *Peptide-pulsed dendritic cell vaccination targeting interleukin-13 receptor alpha2 chain in recurrent malignant glioma patients with HLA-A*24/A*02 allele*. Cytotherapy, 2012. 14(6): p. 733-42.
74. Fong, B., et al., *Monitoring of regulatory T cell frequencies and expression of CTLA-4 on T cells, before and after DC vaccination, can predict survival in GBM patients*. PLoS One, 2012. 7(4): p. e32614.
75. De Vleeschouwer, S., et al., *Stratification according to HGG-IMMUNO RPA model predicts outcome in a large group of patients with relapsed malignant glioma treated by adjuvant postoperative dendritic cell vaccination*. Cancer Immunol Immunother, 2012. 61(11): p. 2105-12.
76. Phuphanich, S., et al., *Phase I trial of a multi-epitope-pulsed dendritic cell vaccine for patients with newly diagnosed glioblastoma*. Cancer Immunol Immunother, 2013. 62(1): p. 125-35.
77. Akiyama, Y., et al., *alpha-type-1 polarized dendritic cell-based vaccination in recurrent high-grade glioma: a phase I clinical trial*. BMC Cancer, 2012. 12: p. 623.
78. Prins, R. M., et al., *Comparison of glioma-associated antigen peptide-loaded versus autologous tumor lysate-loaded dendritic cell vaccination in malignant glioma patients*. J Immunother, 2013. 36(2): p. 152-7.
79. Shah, A. H., et al., *Dendritic cell vaccine for recurrent high-grade gliomas in pediatric and adult subjects: clinical trial protocol*. Neurosurgery, 2013. 73(5): p. 863-7.
80. Reichardt, V. L., et al., *Idiotype vaccination using dendritic cells after autologous peripheral blood stem cell transplantation for multiple myeloma—a feasibility study*. Blood, 1999. 93(7): p. 2411-9.
81. Lim, S. H. and R. *Bailey-Wood, Idiotypic protein-pulsed dendritic cell vaccination in multiple myeloma*. Int J Cancer, 1999. 83(2): p. 215-22.

82. Motta, M. R., et al., *Generation of dendritic cells from CD14+ monocytes positively selected by immunomagnetic adsorption for multiple myeloma patients enrolled in a clinical trial of anti-idiotype vaccination.* Br J Haematol, 2003. 121(2): p. 240-50.
83. Reichardt, V. L., et al., *Idiotype vaccination of multiple myeloma patients using monocyte-derived dendritic cells.* Haematologica, 2003. 88(10): p. 1139-49.
84. Guardino, A. E., et al., *Production of myeloid dendritic cells (DC) pulsed with tumor— specific idiotype protein for vaccination of patients with multiple myeloma.* Cytotherapy, 2006. 8(3): p. 277-89.
85. Lacy, M. Q., et al., *Idiotype-pulsed antigen presenting cells following autologous transplantation for multiple myeloma may be associated with prolonged survival.* Am J Hematol, 2009. 84(12): p. 799-802.
86. Yi, Q., et al., *Optimizing dendritic cell-based immunotherapy in multiple myeloma: intranodal injections of idiotype pulsed CD40 ligand-matured vaccines led to induction of type-1 and cytotoxic T-cell immune responses in patients.* Br J Haematol, 2010. 150(5): p. 554-64.
87. Rollig, C., et al., *Induction of cellular immune responses in patients with stage-I multiple myeloma after vaccination with autologous idiotype-pulsed dendritic cells.* J Immunother, 2011. 34(1): p. 100-6.
88. Zahradova, L., et al., *Efficacy and safety of Id-protein-loaded dendritic cell vaccine in patients with multiple myeloma—phase II study results.* Neoplasma, 2012. 59(4): p. 440-9.
89. Timmerman, J. M., et al., *Idiotype pulsed dendritic cell vaccination for B-cell lymphoma: clinical and immune responses in 35 patients.* Blood, 2002. 99(5): p. 1517-26.
90. Maier, T., et al., *Vaccination of patients with cutaneous T-cell lymphoma using intranodal injection of autologous tumor-lysate-pulsed dendritic cells.* Blood, 2003. 102(7): p. 2338-44.
91. Di Nicola, M., et al., *Vaccination with autologous tumor-loaded dendritic cells induces clinical and immunologic responses in indolent B-cell lymphoma patients with relapsed and measurable disease: a pilot study.* Blood, 2009. 113(1): p. 18-27.
92. Hus, I., et al., *Allogeneic dendritic cells pulsed with tumor lysates or apoptotic bodies as immunotherapy for patients with early-stage B-cell chronic lymphocytic leukemia.* Leukemia, 2005. 19(9): p. 1621-7.
93. Li, L., et al., *Immunotherapy for patients with acute myeloid leukemia using autologous dendritic cells generated from leukemic blasts.* Int J Oncol, 2006. 28(4): p. 855-61.
94. Roddie, H., et al., *Phase I/II study of vaccination with dendritic-like leukaemia cells for the immunotherapy of acute myeloid leukaemia.* Br J Haematol, 2006. 133(2): p. 152-7.
95. Litzow, M. R., et al., *Testing the safety of clinical-grade mature autologous myeloid DC in a phase I clinical immunotherapy trial of CML.* Cytotherapy, 2006. 8(3): p. 290-8.
96. Westermann, J., et al., *Vaccination with autologous non-irradiated dendritic cells in patients with bcr/abl+ chronic myeloid leukaemia.* Br J Haematol, 2007. 137(4): p. 297-306.
97. Hus, I., et al., *Vaccination of B-CLL patients with autologous dendritic cells can change the frequency of leukemia antigen-specific CD8+ T cells as well as CD4+ CD25+FoxP3+ regulatory T cells toward an antileukemia response.* Leukemia, 2008. 22(5): p. 1007-17.
98. Palma, M., et al., *Development of a dendritic cell-based vaccine for chronic lymphocytic leukemia.* Cancer Immunol Immunother, 2008. 57(11): p. 1705-10.
99. Van Tendeloo, V. F., et al., *Induction of complete and molecular remissions in acute myeloid leukemia by Wilms' tumor 1 antigen-targeted dendritic cell vaccination.* Proc Natl Acad Sci USA, 2010. 107(31): p. 13824-9.
100. Iwashita, Y., et al., *A phase I study of autologous dendritic cell-based immunotherapy for patients with unresectable primary liver cancer.* Cancer Immunol Immunother, 2003. 52(3): p. 155-61.
101. Lee, W. C., et al., *Vaccination of advanced hepatocellular carcinoma patients with tumor lysate-pulsed dendritic cells: a clinical trial.* J Immunother, 2005. 28(5): p. 496-504.
102. Butterfield, L. H., et al., *A phase I/II trial testing immunization of hepatocellular carcinoma patients with dendritic cells pulsed with four alpha-fetoprotein peptides.* Clin Cancer Res, 2006. 12(9): p. 2817-25.
103. Palmer, D. H., et al., *A phase II study of adoptive immunotherapy using dendritic cells pulsed with tumor lysate in patients with hepatocellular carcinoma.* Hepatology, 2009. 49(1): p. 124-32.
104. El Ansary, M., et al., *Immunotherapy by autologous dendritic cell vaccine in patients with advanced HCC.* J Cancer Res Clin Oncol, 2013. 139(1): p. 39-48.
105. Tada, F., et al., *Phase I/II study of immunotherapy using tumor antigen-pulsed dendritic cells in patients with hepatocellular carcinoma.* Int J Oncol, 2012. 41(5): p. 1601-9.
106. Ueda, Y., et al., *Dendritic cell-based immunotherapy of cancer with carcinoembryonic antigen-derived, HLA-A24-restricted CTL epitope: Clinical outcomes of 18 patients with metastatic gastrointestinal or lung adenocarcinomas.* Int J Oncol, 2004. 24(4): p. 909-17.
107. Hirschowitz, E. A., et al., *Autologous dendritic cell vaccines for non-small-cell lung cancer.* J Clin Oncol, 2004. 22(14): p. 2808-15.
108. Chang, G. C., et al., *A pilot clinical trial of vaccination with dendritic cells pulsed with autologous tumor cells derived from malignant pleural effusion in patients with late— stage lung carcinoma.* Cancer, 2005. 103(4): p. 763-71.
109. Yannelli, J. R., et al., *The large scale generation of dendritic cells for the immunization of patients with non-small cell lung cancer (NSCLC).* Lung Cancer, 2005. 47(3): p. 337-50.
110. Ishikawa, A., et al., *A phase I study of alpha-galactosylceramide (KRN7000)-pulsed dendritic cells in patients with advanced and recurrent non-small cell lung cancer.* Clin Cancer Res, 2005. 11(5): p. 1910-7.
111. Antonia, S. J., et al., *Combination of p53 cancer vaccine with chemotherapy in patients with extensive stage small cell lung cancer.* Clin Cancer Res, 2006. 12(3 Pt 1): p. 878-87.
112. Perrot, I., et al., *Dendritic cells infiltrating human non-small cell lung cancer are blocked at immature stage.* J Immunol, 2007. 178(5): p. 2763-9.
113. Hirschowitz, E. A., et al., *Immunization of NSCLC patients with antigen-pulsed immature autologous dendritic cells.* Lung Cancer, 2007. 57(3): p. 365-72.
114. Baratelli, F., et al., *Pre-clinical characterization of GMP grade CCL21-gene modified dendritic cells for application in a phase I trial in non-small cell lung cancer.* J Transl Med, 2008. 6: p. 38.

115. Hegmans, J. P., et al., *Consolidative dendritic cell-based immunotherapy elicits cytotoxicity against malignant mesothelioma*. Am J Respir Crit Care Med, 2010. 181(12): p. 1383-90.
116. Um, S. J., et al., *Phase I study of autologous dendritic cell tumor vaccine in patients with non-small cell lung cancer*. Lung Cancer, 2010. 70(2): p. 188-94.
117. Chiappori, A. A., et al., *INGN-225: a dendritic cell-based p53 vaccine (Ad.p53-DC) in small cell lung cancer: observed association between immune response and enhanced chemotherapy effect*. Expert Opin Biol Ther, 2010. 10(6): p. 983-91.
118. Perroud, M. W., Jr., et al., *Mature autologous dendritic cell vaccines in advanced non-small cell lung cancer: a phase I pilot study*. J Exp Clin Cancer Res, 2011. 30: p. 65.
119. Skachkova, O. V., et al., *Immunological markers of anti-tumor dendritic cells vaccine efficiency in patients with non-small cell lung cancer*. Exp Oncol, 2013. 35(2): p. 109-13.
120. Hernando, J. J., et al., *Vaccination with autologous tumour antigen pulsed dendritic cells in advanced gynaecological malignancies: clinical and immunological evaluation of a phase I trial*. Cancer Immunol Immunother, 2002. 51(1): p. 45-52.
121. Rahma, O. E., et al., *A gynecologic oncology group phase II trial of two p53 peptide vaccine approaches: subcutaneous injection and intravenous pulsed dendritic cells in high recurrence risk ovarian cancer patients*. Cancer Immunol Immunother, 2012. 61(3): p. 373-84.
122. Chu, C. S., et al., *Phase I/II randomized trial of dendritic cell vaccination with or without cyclophosphamide for consolidation therapy of advanced ovarian cancer in first or second remission*. Cancer Immunol Immunother, 2012. 61(5): p. 629-41.
123. Kandalaft, L. E., et al., *A Phase I vaccine trial using dendritic cells pulsed with autologous oxidized lysate for recurrent ovarian cancer*. J Transl Med, 2013. 11: p. 149.
124. Lepisto, A. J., et al., *A phase I/II study of a MUC1 peptide pulsed autologous dendritic cell vaccine as adjuvant therapy in patients with resected pancreatic and biliary tumors*. Cancer Ther, 2008. 6(B): p. 955-964.
125. Rong, Y., et al., *A phase I pilot trial of MUC1-peptide-pulsed dendritic cells in the treatment of advanced pancreatic cancer*. Clin Exp Med, 2012. 12(3): p. 173-80.
126. Endo, H., et al., *Phase I trial of preoperative intratumoral injection of immature dendritic cells and OK-432 for resectable pancreatic cancer patients*. J Hepatobiliary Pancreat Sci, 2012. 19(4): p. 465-75.
127. Jackson, L., et al., *Adult mesenchymal stem cells: differentiation potential and therapeutic applications*. J Postgrad Med, 2007. 53(2): p. 121-7.
128. Pittenger, M. F., et al., *Multilineage potential of adult human mesenchymal stem cells*. Science, 1999. 284 (5411): p. 143-7.
129. Banas, A., et al., *Rapid hepatic fate specification of adipose-derived stem cells and their therapeutic potential for liver failure*. J Gastroenterol Hepatol, 2009. 24(1): p. 70-7.
130. Lee, K. D., et al., *In vitro hepatic differentiation of human mesenchymal stem cells*. Hepatology, 2004. 40(6): p. 1275-84.
131. Cho, K. A., et al., *Mesenchymal stem cells showed the highest potential for the regeneration of injured liver tissue compared with other subpopulations of the bone marrow*. Cell Biol Int, 2009. 33(7): p. 772-7.
132. Hong, S. H., et al., *In vitro differentiation of human umbilical cord blood-derived mesenchymal stem cells into hepatocyte-like cells*. Biochem Biophys Res Commun, 2005. 330(4): p. 1153-61.
133. Ishikawa, T., et al., *Stem cells for hepatic regeneration: the role of adipose tissue derived mesenchymal stem cells*. Curr Stem Cell Res Ther, 2010. 5(2): p. 182-9.
134. Seo, M. J., et al., *Differentiation of human adipose stromal cells into hepatic lineage in vitro and in vivo*. Biochem Biophys Res Commun, 2005. 328(1): p. 258-64.
135. Crisan, M., et al., *A perivascular origin for mesenchymal stem cells in multiple human organs*. Cell Stem Cell, 2008. 3(3): p. 301-13.
136. Tavian, M. and B. Peault, *Embryonic development of the human hematopoietic system*. Int J Dev Biol, 2005. 49(2-3): p. 243-50.
137. Peault, B., et al., *Stem and progenitor cells in skeletal muscle development, maintenance, and therapy*. Mol Ther, 2007. 15(5): p. 867-77.
138. Aggarwal, S. and M. F. Pittenger, *Human mesenchymal stem cells modulate allogeneic immune cell responses*. Blood, 2005. 105(4): p. 1815-22.
139. Caplan, A. I., *Adult mesenchymal stem cells for tissue engineering versus regenerative medicine*. J Cell Physiol, 2007. 213(2): p. 341-7.
140. Chamberlain, G., et al., *Concise review: mesenchymal stem cells: their phenotype, differentiation capacity, immunological features, and potential for homing*. Stem Cells, 2007. 25(11): p. 2739-49.
141. Banas, A., et al., *IFATS collection: in vivo therapeutic potential of human adipose tissue mesenchymal stem cells after transplantation into mice with liver injury*. Stem Cells, 2008. 26(10): p. 2705-12.
142. Kharaziha, P., et al., *Improvement of liver function in liver cirrhosis patients after autologous mesenchymal stem cell injection: a phase I-II clinical trial*. Eur J Gastroenterol Hepatol, 2009. 21(10): p. 1199-205.
143. Kuo, T. K., et al., *Stem cell therapy for liver disease: parameters governing the success of using bone marrow mesenchymal stem cells*. Gastroenterology, 2008. 134(7): p. 2111-21, 2121 e1-3.
144. Chang, Y. J., et al., *Mesenchymal stem cells facilitate recovery from chemically induced liver damage and decrease liver fibrosis*. Life Sci, 2009. 85(13-14): p. 517-25.
145. Lu, L. L., et al., *Isolation and characterization of human umbilical cord mesenchymal stem cells with hematopoiesis-supportive function and other potentials*. Haematologica, 2006. 91(8): p. 1017-26.
146. Mohamadnejad, M., et al., *Phase 1 trial of autologous bone marrow mesenchymal stem cell transplantation in patients with decompensated liver cirrhosis*. Arch Iran Med, 2007. 10(4): p. 459-66.
147. Terai, S., et al., *Improved liver function in patients with liver cirrhosis after autologous bone marrow cell infusion therapy*. Stem Cells, 2006. 24(10): p. 2292-8.
148. Chang, C. J., et al., *Placenta-derived multipotent cells exhibit immunosuppressive properties that are enhanced in the presence of interferon-gamma*. Stem Cells, 2006. 24(11): p. 2466-77.
149. Iyer, S. S. and M. Rojas, *Anti-inflammatory effects of mesenchymal stem cells: novel concept for future therapies*. Expert Opin Biol Ther, 2008. 8(5): p. 569-81.
150. Nauta, A. J. and W. E. Fibbe, *Immunomodulatory properties of mesenchymal stromal cells*. Blood, 2007. 110(10): p. 3499-506.

151. Uccelli, A., V. Pistoia, and L. Moretta, *Mesenchymal stem cells: a new strategy for immunosuppression?* Trends Immunol, 2007. 28(5): p. 219-26.
152. Wolbank, S., et al., *Dose-dependent immunomodulatory effect of human stem cells from amniotic membrane: a comparison with human mesenchymal stem cells from adipose tissue.* Tissue Eng, 2007. 13(6): p. 1173-83.
153. Wolf, D. and A. M. Wolf, *Mesenchymal stem cells as cellular immunosuppressants.* Lancet, 2008. 371(9624): p. 1553-4.
154. Shi, M., Z. W. Liu, and F. S. Wang, *Immunomodulatory properties and therapeutic application of mesenchymal stem cells.* Clin Exp Immunol, 2011. 164(1): p. 1-8.
155. Sordi, V. and L. Piemonti, *Therapeutic plasticity of stem cells and allograft tolerance.* Cytotherapy, 2011. 13(6): p. 647-60.
156. Popp, F. C., et al., *Mesenchymal stem cells as immunomodulators after liver transplantation.* Liver Transpl, 2009. 15(10): p. 1192-8.
157. Friedenstein, A. J., R. K. Chailakhjan, and K. S. Lalykina, *The development of fibroblast colonies in monolayer cultures of guinea-pig bone marrow and spleen cells.* Cell Tissue Kinet, 1970. 3(4): p. 393-403.
158. Friedenstein, A. J., et al., *Stromal cells responsible for transferring the microenvironment of the hemopoietic tissues. Cloning in vitro and retransplantation in vivo.* Transplantation, 1974. 17(4): p. 331-40.
159. Caplan, A. I., *Molecular and cellular differentiation of muscle, cartilage, and bone in the developing limb.* Prog Clin Biol Res, 1986. 217B: p. 307-18.
160. Caplan, A. I., *Mesenchymal stem cells.* J Orthop Res, 1991. 9(5): p. 641-50.
161. Kopen, G. C., D. J. Prockop, and D. G. Phinney, *Marrow stromal cells migrate throughout forebrain and cerebellum, and they differentiate into astrocytes after injection into neonatal mouse brains.* Proc Natl Acad Sci USA, 1999. 96(19): p. 10711-6.
162. Petersen, B. E., et al., *Bone marrow as a potential source of hepatic oval cells.* Science, 1999. 284(5417): p. 1168-70.
163. Teratani, T., et al., *Direct hepatic fate specification from mouse embryonic stem cells.* Hepatology, 2005. 41(4): p. 836-46.
164. Le Blanc, K. and O. Ringden, *Immunomodulation by mesenchymal stem cells and clinical experience.* J Intern Med, 2007. 262(5): p. 509-25.
165. Keyser, K. A., K. E. Beagles, and H. P. Kiem, *Comparison of mesenchymal stem cells from different tissues to suppress T-cell activation.* Cell Transplant, 2007. 16(5): p. 555-62.
166. Le Blanc, K., et al., *Mesenchymal stem cells for treatment of steroid-resistant, severe, acute graft-versus-host disease: a phase II study.* Lancet, 2008. 371(9624): p. 1579-86.
167. Ning, H., et al., *The correlation between cotransplantation of mesenchymal stem cells and higher recurrence rate in hematologic malignancy patients: outcome of a pilot clinical study.* Leukemia, 2008. 22(3): p. 593-9.
168. Ball, L., et al., *Third party mesenchymal stromal cell infusions fail to induce tissue repair despite successful control of severe grade IV acute graft-versus-host disease in a child with juvenile myelo-monocytic leukemia.* Leukemia, 2008. 22(6): p. 1256-7.
169. Ringden, O., et al., *Mesenchymal stem cells for treatment of therapy-resistant graft-versus-host disease.* Transplantation, 2006. 81(10): p. 1390-7.
170. Le Blanc, K., et al., *Treatment of severe acute graft-versus-host disease with third party haploidentical mesenchymal stem cells.* Lancet, 2004. 363(9419): p. 1439-41.
171. Muller, I., et al., *Application of multipotent mesenchymal stromal cells in pediatric patients following allogeneic stem cell transplantation.* Blood Cells Mol Dis, 2008. 40(1): p. 25-32.
172. Horwitz, E. M., et al., *Isolated allogeneic bone marrow-derived mesenchymal cells engraft and stimulate growth in children with osteo genesis imperfecta: Implications for cell therapy of bone.* Proc Natl Acad Sci USA, 2002. 99(13): p. 8932-7.
173. Koc, O. N., et al., *Allogeneic mesenchymal stem cell infusion for treatment of metachromatic leukodystrophy (MLD) and Hurler syndrome (MPS-IH).* Bone Marrow Transplant, 2002. 30(4): p. 215-22.
174. Le Blanc, K., et al., *Transplantation of mesenchymal stem cells to enhance engraftment of hematopoietic stem cells.* Leukemia, 2007. 21(8): p. 1733-8.
175. Lazarus, H. M., et al., *Cotransplantation of HLA-identical sibling culture-expanded mesenchymal stem cells and hematopoietic stem cells in hematologic malignancy patients.* Biol Blood Marrow Transplant, 2005. 11(5): p. 389-98.
176. Ball, L. M., et al., *Cotransplantation of ex vivo expanded mesenchymal stem cells accelerates lymphocyte recovery and may reduce the risk of graft failure in haploidentical hematopoietic stem-cell transplantation.* Blood, 2007. 110(7): p. 2764-7.
177. http://www.osiristx.com/pdf/PR%2039%2025Mar07%20Provacel %20Positive %2 OResults.pdf.
178. Kurtzberg, J., et al., *Allogeneic human mesenchymal stem cell therapy (remestemcel-L, Prochymal) as a rescue agent for severe refractory acute graft-versus-host disease in pediatric patients.* Biol Blood Marrow Transplant, 2014. 20(2): p. 229-35.
179. Kellathur, S. N. and H. X. Lou, *Cell and tissue therapy regulation: worldwide status and harmonization.* Biologicals, 2012. 40(3): p. 222-4.
180. Ahmadi, M., et al., *Bone marrow mesenchymal stem cells and their conditioned media could potentially ameliorate ovalbumin-induced asthmatic changes.* Biomed Pharmacother, 2016. 85: p. 28-40.
181. Nemunaitis, J., et al., *Human marrow stromal cells: response to interleukin-6 (IL-6) and control of IL-6 expression.* Blood, 1989. 74(6): p. 1929-35.
182. Sadovnikova, E. Y., et al., *Induction of hematopoietic microenvironment by the extracellular matrix from long-term bone marrow cultures.* Ann Hematol, 1991. 62(5): p. 160-4.
183. Lazarus, H. M., et al., *Ex vivo expansion and subsequent infusion of human bone marrow-derived stromal progenitor cells (mesenchymal progenitor cells): implications for therapeutic use.* Bone Marrow Transplant, 1995. 16(4): p. 557-64.
184. Yoo, J. U., et al., *The chondrogenic potential of human bone-marrow-derived mesenchymal progenitor cells.* J Bone Joint Surg Am, 1998. 80(12): p. 1745-57.
185. Fleming, J. E., Jr., et al., *Monoclonal antibody against adult marrow-derived mesenchymal stem cells recognizes developing vasculature in embryonic human skin.* Dev Dyn, 1998. 212(1): p. 119-32.
186. Ghilzon, R., C. A. McCulloch, and R. Zohar, *Stromal mesenchymal progenitor cells.* Leuk Lymphoma, 1999. 32(3-4): p. 211-21.

187. De Cesaris, V., et al., *Isolation, proliferation and characterization of endometrial canine stem cells.* Reprod Domest Anim, 2016.
188. Van Pham, P., et al., *Isolation and proliferation of umbilical cord tissue derived mesenchymal stem cells for clinical applications.* Cell Tissue Bank, 2016. 17(2): p. 289-302.
189. Zhao, G., et al., *Large-scale expansion of Wharton's jelly-derived mesenchymal stem cells on gelatin microbeads, with retention of self-renewal and multipotency characteristics and the capacity for enhancing skin wound healing.* Stem Cell Res Ther, 2015. 6: p. 38.
190. Huang, P., et al., *Differentiation of human umbilical cord Wharton's jelly-derived mesenchymal stem cells into germ-like cells in vitro.* J Cell Biochem, 2010. 109(4): p. 747-54.
191. Wang, S. J., et al., *Chondrogenic Potential of Peripheral Blood Derived Mesenchymal Stem Cells Seeded on Demineralized Cancellous Bone Scaffolds.* Sci Rep, 2016. 6: p. 36400.
192. Fazeli, Z., M. D. Omrani, and S. M. Ghaderian, *CD29/CD184 expression analysis provides a signature for identification of neuronal like cells differentiated from PBMSCs.* Neurosci Lett, 2016. 630: p. 189-93.
193. Wu, G., et al., *Osteogenesis of peripheral blood mesenchymal stem cells in self assembling peptide nanofiber for healing critical size calvarial bony defect.* Sci Rep, 2015. 5: p. 16681.
194. Shaer, A., et al., *Isolation and characterization of Human Mesenchymal Stromal Cells Derived from Placental Decidua Basalis; Umbilical cord Wharton's Jelly and Amniotic Membrane.* Pak J Med Sci, 2014. 30(5): p. 1022-6.
195. Fu, W. L., C. Y. Zhou, and J. K. Yu, *A new source of mesenchymal stem cells for articular cartilage repair: MSCs derived from mobilized peripheral blood share similar biological characteristics in vitro and chondrogenesis in vivo as MSCs from bone marrow in a rabbit model.* Am J Sports Med, 2014. 42(3): p. 592-601.
196. El-Badawy, A., et al., *Adipose Stem Cells Display Higher Regenerative Capacities and More Adaptable Electro-Kinetic Properties Compared to Bone Marrow-Derived Mesenchymal Stromal Cells.* Sci Rep, 2016. 6: p. 37801.
197. Plock, J. A., et al., *The Influence of Timing and Frequency of Adipose-Derived Mesenchymal Stem Cell Therapy on Immunomodulation Outcomes After Vascularized Composite Allotransplantation.* Transplantation, 2017. 101(1): p. e1-e11.
198. Strauer, B. E., et al., *[Intracoronary, human autologous stem cell transplantation for myocardial regeneration following myocardial infarction].* Dtsch Med Wochenschr, 2001. 126(34-35): p. 932-8.
199. Hamano, K., et al., *Local implantation of autologous bone marrow cells for therapeutic angiogenesis in patients with ischemic heart disease: clinical trial and preliminary results.* Jpn Circ J, 2001. 65(9): p. 845-7.
200. Abdel-Latif, A., et al., *Adult bone marrow-derived cells for cardiac repair: a systematic review and meta-analysis.* Arch Intern Med, 2007. 167(10): p. 989-97.
201. Martin-Rendon, E., et al., *Stem cell treatment for acute myocardial infarction.* Cochrane Database Syst Rev, 2008 (4): p. CD006536.
202. Kang, S., et al., *Effects of intracoronary autologous bone marrow cells on left ventricular function in acute myocardial infarction: a systematic review and meta-analysis for randomized controlled trials.* Coron Artery Dis, 2008. 19(5): p. 327-35.
203. Cheng, Z., et al., *Targeted migration of mesenchymal stem cells modified with CXCR4 gene to infarcted myocardium improves cardiac performance.* Mol Ther, 2008. 16(3): p. 571-9.
204. Fisher, S. A., et al., *Meta-Analysis of Cell Therapy Trials for Patients with Heart Failure-An Update.* Circ Res, 2015.
205. Murry C E, e.a., *Haematopoietic stem cells do not transdifferentiate into cardiac myocytes in myocardial infarcts.* Nature, 2004. 429: p. 664-668
206. Balsam L B, e.a., *Haematopoietic stem cells adopt mature haematopoietic fates in ischaemic myocardium.* Nature, 2004. 428: p. 668-673
207. Assmus B, S. V., Teupe C, Britten M, Lehmann R, Dobert N, et al., *Transplantation of cells and regeneration enhancement in acute myocardial infarction (TOPCARE-AMI).* Circulation, 2002. 106: p. 3009-17.
208. Strauer B E, B. M., Zeus T, Kostering M, Hernandez A, Sorg R V, *Repair of infarcted myocardium by autologous intracoronary mononuclear bone marrow cell transplantation in humans.* Circulation, 2002. 106: p. 1913-8.
209. Stamm, C., B. Westphal, H. D. Kleine, *Autologous bone-marrow stem-cell transplantation for myocardial regeneration.* Lancet, 2003. 361: p. 45-46.
210. Patel, A. N., et al., *Ixmyelocel-T for patients with ischaemic heart failure: a prospective randomised double-blind trial.* Lancet, 2016. 387(10036): p. 2412-21.
211. Guijarro, D., et al., *Intramyocardial transplantation of mesenchymal stromal cells for chronic myocardial ischemia and impaired left ventricular function: Results of the MESAMI 1 pilot trial.* Int J Cardiol, 2016. 209: p. 258-65.
212. Mathiasen, A. B., et al., *Bone marrow-derived mesenchymal stromal cell treatment in patients with severe ischaemic heart failure: a randomized placebo-controlled trial (MSC-HF trial).* Eur Heart J, 2015. 36(27): p. 1744-53.
213. Karantalis, V., et al., *Autologous mesenchymal stem cells produce concordant improvements in regional function, tissue perfusion, and fibrotic burden when administered to patients undergoing coronary artery bypass grafting: The Prospective Randomized Study of Mesenchymal Stem Cell Therapy in Patients Undergoing Cardiac Surgery (PROMETHEUS) trial.* Circ Res, 2014. 114(8): p. 1302-10.
214. Viswanathan, C., et al., *Tansplantation of autologous bone marrow derived mesenchymal stem cells transepicardially in patients undergoing coronary bypass surgery.* Indian Heart J, 2010. 62(1): p. 43-8.
215. Heldman, A. W., et al., *Transendocardial mesenchymal stem cells and mononuclear bone marrow cells for ischemic cardiomyopathy: the TAC-HFT randomized trial.* JAMA, 2014. 311(1): p. 62-73.
216. Suncion, V. Y., et al., *Does transendocardial injection of mesenchymal stem cells improve myocardial function locally or globally?: An analysis from the Percutaneous Stem Cell Injection Delivery Effects on Neomyogenesis (POSEIDON) randomized trial.* Circ Res, 2014. 114(8): p. 1292-301.
217. Mathiasen, A. B., et al., *Autotransplantation of mesenchymal stromal cells from bone-marrow to heart in patients with severe stable coronary artery disease and refractory angina final 3-year follow-up.* Int J Cardiol, 2013. 170(2): p. 246-51.
218. Bartunek, J., et al., *Cardiopoietic stem cell therapy in heart failure: the C-CURE (Cardiopoietic stem Cell* therapy in heart failURE) multicenter randomized trial with lineage-specified biologics. J Am Coll Cardiol, 2013. 61(23): p. 2329-38.
219. Haack-Sorensen, M., et al., *Direct intramyocardial mesenchymal stromal cell injections in patients with severe refractory angina: one-year follow-up.* Cell Transplant, 2013. 22(3): p. 521-8.
220. Chin, S. P., et al., *Intramyocardial and intracoronary autologous bone marrow-derived mesenchymal stromal cell treatment in chronic severe dilated cardiomyopathy.* Cytotherapy, 2011. 13(7): p. 814-21.
221. Williams, A. R., et al., *Intramyocardial stem cell injection in patients with ischemic cardiomyopathy: functional recovery and reverse remodeling.* Circ Res, 2011. 108(7): p. 792-6.
222. Zeinaloo, A., et al., *Intracoronary administration of autologous mesenchymal stem cells in a critically ill patient with dilated cardiomyopathy.* Pediatr Transplant, 2011. 15(8): p. E183-6.
223. Lasala, G. P., et al., *Combination stem cell therapy for the treatment of medically refractory coronary ischemia: a Phase I study.* Cardiovasc Revasc Med, 2011. 12(1): p. 29-34.
224. Anastasiadis, K., et al., *Implantation of a Novel Allogeneic Mesenchymal Precursor Cell Type in Patients with Ischemic Cardiomyopathy Undergoing Coronary Artery Bypass Grafting: an Open Label Phase Ha Trial.* J Cardiovasc Transl Res, 2016. 9(3): p. 202-13.
225. Perin, E. C., et al., *A Phase II Dose-Escalation Study of Allogeneic Mesenchymal Precursor Cells in Patients With Ischemic or Nonischemic Heart Failure.* Circ Res, 2015. 117(6): p. 576-84.
226. Premer, C., et al., *Allogeneic Mesenchymal Stem Cells Restore Endothelial Function in Heart Failure by Stimulating Endothelial Progenitor Cells.* EBioMedicine, 2015. 2(5): p. 467-75.
227. Ascheim, D. D., et al., *Mesenchymal precursor cells as adjunctive therapy in recipients of contemporary left ventricular assist devices.* Circulation, 2014. 129(22): p. 2287-96.
228. Hare, J. M., et al., *Comparison of allogeneic vs autologous bone marrow-derived mesenchymal stem cells delivered by transendocardial injection in patients with ischemic cardiomyopathy: the POSEIDON randomized trial.* JAMA, 2012. 308(22): p. 2369-79.
229. Zhao, X. F., et al., *Clinical observation of umbilical cord mesenchymal stem cell treatment of severe systolic heart failure.* Genet Mol Res, 2015. 14(2): p. 3010-7.
230. Li, X., et al., *Safety and efficacy of intracoronary human umbilical cord-derived mesenchymal stem cell treatment for very old patients with coronary chronic total occlusion.* Curr Pharm Des, 2015. 21(11): p. 1426-32.
231. Ichim, T. E., et al., *Combination stem cell therapy for heart failure.* Int Arch Med, 2010. 3(1): p. 5.
232. Ichim, T. E., et al., *Placental mesenchymal and cord blood stem cell therapy for dilated cardiomyopathy.* Reprod Biomed Online, 2008. 16(6): p. 898-905.
233. Lee, J. W., et al., *A randomized, open-label, multicenter trial for the safety and efficacy of adult mesenchymal stem cells after acute myocardial infarction.* J Korean Med Sci, 2014. 29(1): p. 23-31.
234. Rodrigo, S. F., et al., *Intramyocardial injection of autologous bone marrow-derived ex vivo expanded mesenchymal stem cells in acute myocardial infarction patients is feasible and safe up to 5 years of follow-up.* J Cardiovasc Transl Res, 2013. 6(5): p. 816-25.
235. Straburzynska-Migaj, E., et al., *Exercise capacity, arrhythmic risk profile, and pulmonary function is not influenced by intracoronary injection of bone marrow stem cells in patients with acute myocardial infarction.* Int J Cardiol, 2012. 159(2): p. 134-8.
236. Hare, J. M., et al., *A randomized, double-blind, placebo-controlled, dose-escalation study of intravenous adult human mesenchymal stem cells (prochymal) after acute myocardial infarction.* J Am Coll Cardiol, 2009. 54(24): p. 2277-86.
237. Chullikana, A., et al., *Randomized, double-blind, phase I/II study of intravenous allogeneic mesenchymal stromal cells in acute myocardial infarction.* Cytotherapy, 2015. 17(3): p. 250-61.
238. Gao, L. R., et al., *Intracoronary infusion of Wharton's jelly-derived mesenchymal stem cells in acute myocardial infarction: double-blind, randomized controlled trial.* BMC Med, 2015. 13: p. 162.
239. Musialek, P., et al., *Myocardial regeneration strategy using Wharton's jelly mesenchymal stem cells as an off-the-shelf 'unlimited' therapeutic agent: results from the Acute Myocardial Infarction First-in-Man Study.* Postepy Kardiol Interwencyjnej, 2015. 11(2): p. 100-7.

The invention claimed is:

1. A method of preventing, and/or inhibiting, and/or reversing heart failure, comprising the steps of:
 a) identifying a patient suffering from or at risk of heart failure;
 b) extracting T regulatory cells from a subject;
 c) providing mesenchymal stem cells derived from a source selected from the group consisting of: placental tissue, amniotic membrane, umbilical cord tissue, fallopian tube tissue, and subepithelial umbilical cord tissue;
 d) contacting said mesenchymal stem cells with interferon gamma in vitro and generating a mesenchymal stem cell conditioned media (MSC-CM);
 e) culturing said T regulatory cells with said MSC-CM in vitro in the presence of interleukin 2 in a manner so that the MSC-CM endows onto said T regulatory cells properties capable of preventing, inhibiting and/or reversing heart failure; and
 f) administering said cultured T regulatory cells into said patient.

2. The method of claim 1, wherein the patient has suffered from a myocardial infarction.

3. The method of claim 1, wherein the patient suffers from angina.

4. The method of claim 3, wherein the patient's angina is ameliorated after administration of the T regulatory cells.

5. The method of claim 1, wherein the MSC-CM expresses higher levels of hepatocyte growth factor (HGF) than normal.

6. The method of claim 1, wherein the cultured T regulatory cells are CD4+, CD25+, Helios+, and FOXP3+.

7. The method of claim 1, wherein the T regulatory cells are autologous to the patient.

8. The method of claim 1, wherein the mesenchymal stem cells are derived from umbilical cord tissue.

* * * * *